US007939494B2

(12) United States Patent
Khan et al.

(10) Patent No.: US 7,939,494 B2
(45) Date of Patent: May 10, 2011

(54) METHOD FOR ADMINISTERING GLP-1 MOLECULES

(75) Inventors: Mohammed Amin Khan, Palo Alto, CA (US); Bryan Edward Jones, San Diego, CA (US); John McNeill McGill, Greenwood, IN (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 0 days.

(21) Appl. No.: 12/421,590

(22) Filed: Apr. 9, 2009

(65) Prior Publication Data
US 2009/0286735 A1 Nov. 19, 2009

Related U.S. Application Data

(63) Continuation of application No. 10/504,717, filed as application No. PCT/US03/03111 on Feb. 7, 2003, now abandoned.

(60) Provisional application No. 60/358,184, filed on Feb. 20, 2002.

(51) Int. Cl.
*A61K 38/00* (2006.01)

(52) U.S. Cl. ........................................ 514/5.3; 514/364

(58) Field of Classification Search ........................ None
See application file for complete search history.

(56) References Cited

U.S. PATENT DOCUMENTS

| 5,118,666 A | 6/1992 | Habener |
| 5,120,712 A | 6/1992 | Habener |
| 5,122,539 A | 6/1992 | Abraham et al. |
| 5,238,917 A | 8/1993 | Fujii et al. |
| 5,304,575 A | 4/1994 | Beck |
| 5,424,286 A | 6/1995 | Eng |
| 5,443,841 A | 8/1995 | Milstein et al. |
| 5,447,728 A | 9/1995 | Milstein et al. |
| 5,451,410 A | 9/1995 | Milstein et al. |
| 5,512,549 A | 4/1996 | Chen et al. |
| 5,541,155 A | 7/1996 | Leone-Bay et al. |
| 5,545,618 A | 8/1996 | Buckley et al. |
| 5,578,323 A | 11/1996 | Milstein et al. |
| 5,614,492 A | 3/1997 | Habener |
| 5,629,020 A | 5/1997 | Leone-Bay et al. |
| 5,631,224 A | 5/1997 | Efendic et al. |
| 5,643,957 A | 7/1997 | Leone-Bay et al. |
| 5,650,386 A | 7/1997 | Leone-Bay et al. |
| 5,693,338 A | 12/1997 | Milstein |
| 5,705,483 A | 1/1998 | Galloway et al. |
| 5,714,167 A | 2/1998 | Milstein et al. |
| 5,734,026 A | 3/1998 | Florin-Robertsson et al. |
| 5,766,620 A | 6/1998 | Heiber et al. |
| 5,766,633 A | 6/1998 | Milstein et al. |
| 5,773,647 A | 6/1998 | Leone-Bay et al. |
| 5,780,599 A | 7/1998 | Junker et al. |
| 5,792,451 A | 8/1998 | Sarubbi et al. |
| 5,811,127 A | 9/1998 | Milstein et al. |
| 5,820,881 A | 10/1998 | Milstein |
| 5,837,702 A | 11/1998 | Rovnyak et al. |
| 5,849,322 A | 12/1998 | Ebert et al. |
| 5,863,555 A | 1/1999 | Heiber et al. |
| 5,866,536 A | 2/1999 | Leone-Bay et al. |
| 5,935,601 A | 8/1999 | Leone-Bay et al. |
| 5,955,503 A | 9/1999 | Leone-Bay et al. |
| 5,958,457 A | 9/1999 | Santiago et al. |
| 5,965,121 A | 10/1999 | Leone-Bay et al. |
| 5,976,569 A | 11/1999 | Milstein |
| 5,977,071 A | 11/1999 | Galloway et al. |
| 5,989,539 A | 11/1999 | Leone-Bay et al. |
| 5,990,166 A | 11/1999 | Leone-Bay et al. |
| 6,001,347 A | 12/1999 | Leone-Bay et al. |
| 6,006,753 A | 12/1999 | Efendic |
| 6,009,856 A | 1/2000 | Smith, III et al. |
| 6,071,510 A | 6/2000 | Leone-Bay et al. |
| 6,071,538 A | 6/2000 | Milstein et al. |
| 6,100,298 A | 8/2000 | Leone-Bay et al. |
| 6,180,140 B1 | 1/2001 | Leone-Bay et al. |
| 6,191,102 B1 | 2/2001 | DiMarchi et al. |
| 6,221,367 B1 | 4/2001 | Milstein et al. |
| 6,242,495 B1 | 6/2001 | Leone-Bay et al. |
| 6,245,359 B1 | 6/2001 | Milstein et al. |
| 6,268,343 B1 | 7/2001 | Knudsen et al. |
| 6,284,727 B1 | 9/2001 | Kim et al. |
| 6,313,088 B1 | 11/2001 | Leone-Bay et al. |
| 6,329,336 B1 | 12/2001 | Bridon et al. |
| 6,344,213 B1 | 2/2002 | Leone-Bay et al. |
| 6,380,357 B2 | 4/2002 | Hermeling et al. |
| 6,428,780 B2 | 8/2002 | Leone-Bay et al. |

(Continued)

FOREIGN PATENT DOCUMENTS

EP 0619322 A2 10/1994

(Continued)

OTHER PUBLICATIONS

Larsen, MD, Jens, et al.: "Glucagon-Like Peptide-Like Peptide-1 Infusion Must Be Maintained for 24 h/day to Obtain Acceptable Glycemia in Type 2 Diabetic Patients Who Are Poorly Controlled on Sulphonylurea Treatment," Diabetes Care, vol. 24, No. 8, Aug. 2001, pp. 1416-1421.
Supplementary European Search Report for EP03707669, Jul. 23, 2009.
Hermann, C., et al.: "Glucagon-like peptide-1 and glucose-dependent insulin-releasing polypeptide plasma levels in response to nutrients," Digestion 1995, vol. 56, No. 2, pp. 117-126.
Aungst, BJ, "Novel Formulation Strategies for Improcing Oral Bioavailability of Drugs with Poor Membrane Permeation or Presystemic Metabolism", Jour. Pharm. Science, 1993, pp. 979-987, vol. 82(10).
Epand, R. M., Mol. Pharmacol., 22:105-108, 1982.
Flint, A., et al., J. Clin. Invest., 101:515-520, 1998.
Gutniak, M., et al., N. E. J. Med., 326(20):1316-1322, 1992.
Holz, G. G., et al., Nature, 361:362-365, 1993.
Kim, Y., et al., Pharm. Res., 12:1664-1670, The Application of Crystal Soaking Technique to Study the Effect of Zinc and Cresol on Insulinotropin Crystals Grown from a Saline Solution, 1995.

(Continued)

*Primary Examiner* — Michael Pak
(74) *Attorney, Agent, or Firm* — Blank Rome LLP

(57) ABSTRACT

The invention relates to formulations that demonstrate the feasibility of oral absorption comprising glucose-like peptide-1 compounds and specified delivery agents, and to methods of stimulating GLP-1 receptor in a subject in need of such stimulation, by administration of the formulation of the present invention.

4 Claims, No Drawings

U.S. PATENT DOCUMENTS

| | | |
|---|---|---|
| 6,514,500 B1 | 2/2003 | Bridon et al. |
| 6,583,111 B1 | 6/2003 | DiMarchi et al. |
| 2004/0147484 A1 | 7/2004 | Boyd et al. |
| 2010/0016229 A1 | 1/2010 | Sarubbi |

FOREIGN PATENT DOCUMENTS

| | | |
|---|---|---|
| EP | 619322 A2 | 10/1994 |
| EP | 0658568 A1 | 6/1995 |
| EP | 0869135 A1 | 10/1998 |
| WO | WO-9325579 A1 | 12/1993 |
| WO | WO-9505848 A1 | 3/1995 |
| WO | 199528920 A1 | 11/1995 |
| WO | WO-9620005 A1 | 7/1996 |
| WO | WO-9630036 A1 | 10/1996 |
| WO | WO-9715296 A1 | 5/1997 |
| WO | WO-9805351 A1 | 2/1998 |
| WO | WO-9808531 A1 | 3/1998 |
| WO | WO-9808871 A1 | 3/1998 |
| WO | WO-9819698 A1 | 5/1998 |
| WO | WO-9820895 A1 | 5/1998 |
| WO | WO-9907404 A1 | 2/1999 |
| WO | WO-9916427 A1 | 4/1999 |
| WO | WO-9925727 A2 | 5/1999 |
| WO | WO-9925728 A1 | 5/1999 |
| WO | WO-9940788 A1 | 8/1999 |
| WO | WO-9943708 A1 | 9/1999 |
| WO | WO-9964060 A1 | 12/1999 |
| WO | WO-007617 A1 | 2/2000 |
| WO | WO-0016797 A2 | 3/2000 |
| WO | WO-0040203 A2 | 7/2000 |
| WO | WO-0047188 A1 | 8/2000 |
| WO | WO-0050386 A1 | 8/2000 |
| WO | WO-0059863 A1 | 10/2000 |
| WO | WO-0132130 A2 | 5/2001 |
| WO | WO-0144199 A1 | 6/2001 |
| WO | WO-0151454 A1 | 7/2001 |
| WO | WO-0202509 A1 | 1/2002 |
| WO | WO-02100338 A2 | 12/2002 |
| WO | WO-03045306 A2 | 6/2003 |
| WO | WO-2004062587 A2 | 7/2004 |

OTHER PUBLICATIONS

Komatsu, R., et al., Diabetes, 38:902-905, 1989.

Leone-Bay, A, et al., "4-(4-Salicyloylaminophenyl)butryic Acids as a Novel Oral Delivery Agent for Recombinant Human Growth Hormone", Abstracts of AM. Chem. Soc., 1996, pp. 1-2, pMEDI6.

Leone-Bay, A, et al., "4-[4-[(2-Hydroxybenzoyl) amino]phenyl] butyric Acid as a Novel Oral Delivery Agent for Recombinant Human Growth Hormone", J. Med. Chem., 1996, pp. 2571-2578, vol. 39.

Leone-Bay, A, et al., "Delivery Agents that facilitate the absorpotion of macromolecular drugs", Curr. Opinion in Drug Discovery and Dev., 1999, pp. 26-32, vol. 2(1).

Leone-Bay, A, et al., "N-Acylated β-Amino Acids as novel Oral Delivery Agents for Proteins", J. Med. Chem., 1995, pp. 4263-4269, vol. 38.

Leone-Bay, A, et al., "Oral Delivery of Biologically Active Parathyroid Hormone", Pharm. Research, 2001, pp. 964-970, vol. 18(7).

Lone Pridal, et al., International Journal of Pharamceutics, 136:53-59, Absorpotion of glucagon-like peptide-1 can be protracted by zinc or protamine, 1996.

Majsov, S., Int. J. Peptide Protein Res., 40-:33-343, 1989.

Mentlein, R, et al., "Dipeptidyl-peptidase IV hydrolyses gastric inhibitory polypeptide, gluacgons-like peptide-1(7-6)amide, peptide histidine methionine and is responsible for their degradation in human serum", Eur. J. Biochem., 1993, pp. 829-835, vol. 214.

Mentlein, R., et al., Eur. J. Biochem., 214:829-835, 1993.

Murakami, T, et al., "Effect of Absorporation Promoters on Subcutaneous Absorption of Human Epidermal Growth Factor in Rats," J. Pharm. Sciences, 1993, pp. 236-239, vol. 82(3).

Naslund, E. et al., Am. J. Clin. Nutr., 68:525-530, 1998.

Naslund, E., et al., Drug News Perspect, 11:92-97, 1998.

Nauck, M. a., et al., Diabestologia, 36:741-744, 1993.

Nauck, M. A., et al., J. Clin. Invest., 91:301-307, 1993.

Orskov, C., Diabestologia, 35: 701-711, 1992.

Orskov, C., et al., J. Biol. Chem., 264(22): 12826-12829, 1989.

Rai et al. Actions of Helodermatidae venom peptides and mammalian glucagon-like peptides on gastric chief cells. Am. Physiol J. 1993, vol. 265, pp. G118-G125, see especially abstract and p. G118.

Stoll, BR, et al., "A mechanistic analyssi of carrier-mediated oral delivery of protein therapeutics", J. Controlled Release, 2000 pp. 217-228, vol. 64.

Suzuki, S., et al., Endocrinology, 125:3109-3114, 1990.

Thorens, B., et al., Diabetes, 42:1219-1225, 1993.

Wang, W., "Oral Protein Drug Delivery", J. Drug Targeting, 1996, pp. 195-232, vol. 4(4).

Non-Final Office Action dated Sep. 1, 2010, issued in U.S. Appl. No. 12/497,373.

SEQUENCE LISTING

```
<160> NUMBER OF SEQ ID NOS: 14

<210> SEQ ID NO 1
<211> LENGTH: 31
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (30)..(30)
<223> OTHER INFORMATION: AMIDATION, if Xaa at 31 is deleted
<220> FEATURE:
<221> NAME/KEY: misc_feature
<222> LOCATION: (31)..(31)
<223> OTHER INFORMATION: Xaa = Gly or is deleted

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 2
<211> LENGTH: 39
<212> TYPE: PRT
<213> ORGANISM: Artificial
<220> FEATURE:
<223> OTHER INFORMATION: Synthetic construct
```

-continued

```
<220> FEATURE:
<221> NAME/KEY: misc_feature
<222> LOCATION: (2)..(2)
<223> OTHER INFORMATION: Xaa is Ala, Gly, Ser, Thr, Leu, Ile, Val, Glu,
      Asp, or Lys
<220> FEATURE:
<221> NAME/KEY: misc_feature
<222> LOCATION: (3)..(3)
<223> OTHER INFORMATION: Xaa is Glu, Asp, or Lys
<220> FEATURE:
<221> NAME/KEY: misc_feature
<222> LOCATION: (5)..(5)
<223> OTHER INFORMATION: Xaa is Thr, Ala, Gly, Ser, Leu, Ile, Val, Glu,
      Asp, or Lys
<220> FEATURE:
<221> NAME/KEY: misc_feature
<222> LOCATION: (8)..(8)
<223> OTHER INFORMATION: Xaa is Ser, Ala, Gly, Thr, Leu, Ile, Val, Glu,
      Asp, or Lys
<220> FEATURE:
<221> NAME/KEY: misc_feature
<222> LOCATION: (10)..(10)
<223> OTHER INFORMATION: Xaa is Val, Ala, Gly, Ser, Thr, Leu, Ile, Tyr,
      Glu, Asp, Trp, or Lys
<220> FEATURE:
<221> NAME/KEY: misc_feature
<222> LOCATION: (11)..(11)
<223> OTHER INFORMATION: Xaa is Ser, Ala, Gly, Thr, Leu, Ile, Val, Glu,
      Asp, or Lys
<220> FEATURE:
<221> NAME/KEY: misc_feature
<222> LOCATION: (12)..(12)
<223> OTHER INFORMATION: Xaa is Ser, Ala, Gly, Thr, Leu, Ile, Val, Glu,
      Asp, Trp, Tyr, or Lys
<220> FEATURE:
<221> NAME/KEY: misc_feature
<222> LOCATION: (13)..(13)
<223> OTHER INFORMATION: Xaa is Tyr, Phe, Trp, Glu, Asp, Gln, or Lys
<220> FEATURE:
<221> NAME/KEY: misc_feature
<222> LOCATION: (14)..(14)
<223> OTHER INFORMATION: Xaa is Leu, Ala, Gly, Ser, Thr, Ile, Val, Glu,
      Asp, Met, Trp, Tyr, or Lys
<220> FEATURE:
<221> NAME/KEY: misc_feature
<222> LOCATION: (15)..(15)
<223> OTHER INFORMATION: Xaa is Glu, Asp, or Lys
<220> FEATURE:
<221> NAME/KEY: misc_feature
<222> LOCATION: (16)..(16)
<223> OTHER INFORMATION: Xaa is Gly, Ala, Ser, Thr, Leu, Ile, Val, Glu,
      Asp, or Lys
<220> FEATURE:
<221> NAME/KEY: misc_feature
<222> LOCATION: (17)..(17)
<223> OTHER INFORMATION: Xaa is Gln, Asn, Arg, Glu, Asp, or Lys
<220> FEATURE:
<221> NAME/KEY: misc_feature
<222> LOCATION: (18)..(18)
<223> OTHER INFORMATION: Xaa is Ala, Gly, Ser, Thr, Leu, Ile, Val, Arg,
      Glu, Asp, or Lys
<220> FEATURE:
<221> NAME/KEY: misc_feature
<222> LOCATION: (19)..(19)
<223> OTHER INFORMATION: Xaa is Ala, Gly, Ser, Thr, Leu, Ile, Val, Glu,
      Asp, or Lys
<220> FEATURE:
<221> NAME/KEY: misc_feature
<222> LOCATION: (20)..(20)
<223> OTHER INFORMATION: Xaa is Lys, Arg, Gln, Glu, Asp, or His
<220> FEATURE:
<221> NAME/KEY: misc_feature
<222> LOCATION: (21)..(21)
<223> OTHER INFORMATION: Xaa is Leu, Glu, Asp, or Lys
<220> FEATURE:
<221> NAME/KEY: misc_feature
<222> LOCATION: (24)..(24)
<223> OTHER INFORMATION: Xaa is Ala, Gly, Ser, Thr, Leu, Ile, Val, Glu,
      Asp, or Lys
<220> FEATURE:
```

```
<221> NAME/KEY: misc_feature
<222> LOCATION: (25)..(25)
<223> OTHER INFORMATION: Xaa is Trp, Phe, Tyr, Glu, Asp, or Lys
<220> FEATURE:
<221> NAME/KEY: misc_feature
<222> LOCATION: (26)..(26)
<223> OTHER INFORMATION: Xaa is Leu, Gly, Ala, Ser, Thr, Ile, Val, Glu,
      Asp, or Lys
<220> FEATURE:
<221> NAME/KEY: misc_feature
<222> LOCATION: (27)..(27)
<223> OTHER INFORMATION: Xaa is Val, Gly, Ala, Ser, Thr, Leu, Ile, Glu,
      Asp, or Lys
<220> FEATURE:
<221> NAME/KEY: misc_feature
<222> LOCATION: (28)..(28)
<223> OTHER INFORMATION: Xaa is Asn, Lys, Arg, Glu, Asp, or His
<220> FEATURE:
<221> NAME/KEY: misc_feature
<222> LOCATION: (29)..(29)
<223> OTHER INFORMATION: Xaa is Gly, Ala, Ser, Thr, Leu, Ile, Val, Glu,
      Asp, or Lys
<220> FEATURE:
<221> NAME/KEY: misc_feature
<222> LOCATION: (30)..(30)
<223> OTHER INFORMATION: Xaa is Gly, Arg, Lys, Glu, Asp, or His
<220> FEATURE:
<221> NAME/KEY: misc_feature
<222> LOCATION: (31)..(31)
<223> OTHER INFORMATION: Xaa is Pro, Gly, Ala, Ser, Thr, Leu, Ile, Val,
      Glu, Asp, or Lys, or is deleted
<220> FEATURE:
<221> NAME/KEY: misc_feature
<222> LOCATION: (31)..(38)
<223> OTHER INFORMATION: When the amino acid in this position is
      deleted, all subsequent amino acids are deleted.
<220> FEATURE:
<221> NAME/KEY: misc_feature
<222> LOCATION: (32)..(32)
<223> OTHER INFORMATION: Xaa is Ser, Arg, Lys, Glu, Asp, or His, or
      is deleted
<220> FEATURE:
<221> NAME/KEY: misc_feature
<222> LOCATION: (33)..(33)
<223> OTHER INFORMATION: Xaa is Ser, Arg, Lys, Glu, Asp, or His, or
      is deleted
<220> FEATURE:
<221> NAME/KEY: misc_feature
<222> LOCATION: (34)..(34)
<223> OTHER INFORMATION: Xaa is Gly, Asp, Glu, or Lys, or is deleted
<220> FEATURE:
<221> NAME/KEY: misc_feature
<222> LOCATION: (35)..(35)
<223> OTHER INFORMATION: Xaa is Ala, Phe, Trp, Tyr, Glu, Asp, or Lys,
      or is deleted
<220> FEATURE:
<221> NAME/KEY: misc_feature
<222> LOCATION: (36)..(36)
<223> OTHER INFORMATION: Xaa is Ser, Pro, Lys, Glu, or Asp, or is
      deleted
<220> FEATURE:
<221> NAME/KEY: misc_feature
<222> LOCATION: (37)..(37)
<223> OTHER INFORMATION: Xaa is Ser, Pro, Glu, Asp, or Lys, or is
      deleted
<220> FEATURE:
<221> NAME/KEY: misc_feature
<222> LOCATION: (38)..(38)
<223> OTHER INFORMATION: Xaa is Gly, Pro, Glu, Asp, or Lys, or is
      deleted
<220> FEATURE:
<221> NAME/KEY: misc_feature
<222> LOCATION: (39)..(39)
<223> OTHER INFORMATION: Xaa is Ala, Ser, Val, Glu, Asp, or Lys, or
      is deleted
<220> FEATURE:
<221> NAME/KEY: MOD_RES
<222> LOCATION: (39)..(39)
<223> OTHER INFORMATION: AMIDATION: Ala, Ser, Val, Glu, Asp, or Lys in
      this position may be amidated.
```

```
<400> SEQUENCE: 2

His Xaa Xaa Gly Xaa Phe Thr Xaa Asp Xaa Xaa Xaa Xaa Xaa Xaa
1               5                   10                  15

Xaa Xaa Xaa Xaa Xaa Phe Ile Xaa Xaa Xaa Xaa Xaa Xaa Xaa Xaa
                20                  25                  30

Xaa Xaa Xaa Xaa Xaa Xaa Xaa
        35

<210> SEQ ID NO 3
<211> LENGTH: 31
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is L-histidine, D-histidine,
      desaminohistidine, 2-aminohistidine, beta-hydroxyhistidine,
      homohistidine, alpha-fluoromethylhistidine or
      alpha-methylhistidine
<220> FEATURE:
<221> NAME/KEY: misc_feature
<222> LOCATION: (2)..(2)
<223> OTHER INFORMATION: Xaa is Gly, Ala, Val, Leu, Ile, Ser, or Thr
<220> FEATURE:
<221> NAME/KEY: misc_feature
<222> LOCATION: (3)..(3)
<223> OTHER INFORMATION: Xaa is Thr, Ser, Arg, Lys, Trp, Phe, Tyr, Glu,
      or His
<220> FEATURE:
<221> NAME/KEY: misc_feature
<222> LOCATION: (5)..(5)
<223> OTHER INFORMATION: Xaa is Asp, Glu, Arg, Thr, Ala, Lys, or His
<220> FEATURE:
<221> NAME/KEY: misc_feature
<222> LOCATION: (6)..(6)
<223> OTHER INFORMATION: Xaa is His, Trp, Phe, or Tyr
<220> FEATURE:
<221> NAME/KEY: misc_feature
<222> LOCATION: (10)..(10)
<223> OTHER INFORMATION: Xaa is Leu, Ser, Thr, Trp, His, Phe, Asp, Val,
      Tyr, Glu, or Ala
<220> FEATURE:
<221> NAME/KEY: misc_feature
<222> LOCATION: (12)..(12)
<223> OTHER INFORMATION: Xaa is His, Pro, Asp, Glu, Arg, Ser, Ala, or
      Lys
<220> FEATURE:
<221> NAME/KEY: misc_feature
<222> LOCATION: (13)..(13)
<223> OTHER INFORMATION: Xaa is Gly, Asp, Glu, Gln, Asn, Lys, Arg, or
      Cys
<220> FEATURE:
<221> NAME/KEY: misc_feature
<222> LOCATION: (17)..(17)
<223> OTHER INFORMATION: Xaa is His, Asp, Lys, Glu, Gln, or Arg
<220> FEATURE:
<221> NAME/KEY: misc_feature
<222> LOCATION: (18)..(18)
<223> OTHER INFORMATION: Xaa is Glu, Arg, Ala, or Lys
<220> FEATURE:
<221> NAME/KEY: misc_feature
<222> LOCATION: (20)..(20)
<223> OTHER INFORMATION: Xaa is Trp, Tyr, Phe, Asp, Lys, Glu, or His
<220> FEATURE:
<221> NAME/KEY: misc_feature
<222> LOCATION: (21)..(21)
<223> OTHER INFORMATION: Xaa is Ala, Glu, His, Phe, Tyr, Trp, Arg, or
      Lys
<220> FEATURE:
<221> NAME/KEY: misc_feature
<222> LOCATION: (24)..(24)
<223> OTHER INFORMATION: Xaa is Ala, Glu, Asp, Ser, or His
<220> FEATURE:
```

```
<221> NAME/KEY: misc_feature
<222> LOCATION: (25)..(25)
<223> OTHER INFORMATION: Xaa is Asp, Glu, Ser, Thr, Arg, Trp, or Lys
<220> FEATURE:
<221> NAME/KEY: misc_feature
<222> LOCATION: (27)..(27)
<223> OTHER INFORMATION: Xaa is Asp, Arg, Val, Lys, Ala, Gly, or Glu
<220> FEATURE:
<221> NAME/KEY: misc_feature
<222> LOCATION: (28)..(28)
<223> OTHER INFORMATION: Xaa is Glu, Lys, or Asp
<220> FEATURE:
<221> NAME/KEY: misc_feature
<222> LOCATION: (29)..(29)
<223> OTHER INFORMATION: Xaa is Thr, Ser, Lys, Arg, Trp, Tyr, Phe, Asp,
      Gly, Pro, His, or Glu
<220> FEATURE:
<221> NAME/KEY: misc_feature
<222> LOCATION: (30)..(30)
<223> OTHER INFORMATION: Xaa is Thr, Ser, Asp, Trp, Tyr, Phe, Arg, Glu,
      or His
<220> FEATURE:
<221> NAME/KEY: misc_feature
<222> LOCATION: (31)..(31)
<223> OTHER INFORMATION: Xaa is Lys, Arg, Thr, Ser, Glu, Asp, Trp, Tyr,
      Phe, His, Gly, Gly-Pro, or is deleted

<400> SEQUENCE: 3

Xaa Xaa Xaa Gly Xaa Xaa Thr Ser Asp Xaa Ser Xaa Xaa Leu Glu Gly
1               5                   10                  15

Xaa Xaa Ala Xaa Xaa Phe Ile Xaa Xaa Leu Xaa Xaa Xaa Xaa Xaa
            20                  25                  30

<210> SEQ ID NO 4
<211> LENGTH: 31
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is L-histidine, D-histidine,
      desaminohistidine, 2-aminohistidine, beta-hydroxyhistidine,
      homohistidine, alpha-fluoromethylhistidine or
      alpha-methylhistidine
<220> FEATURE:
<221> NAME/KEY: misc_feature
<222> LOCATION: (2)..(2)
<223> OTHER INFORMATION: Xaa is Gly, Ala, Val, Leu, Ile, Ser, or Thr
<220> FEATURE:
<221> NAME/KEY: misc_feature
<222> LOCATION: (5)..(5)
<223> OTHER INFORMATION: Xaa is Asp, Glu, Arg, Thr, Ala, Lys, or His
<220> FEATURE:
<221> NAME/KEY: misc_feature
<222> LOCATION: (6)..(6)
<223> OTHER INFORMATION: Xaa is His, Trp, Phe, or Tyr
<220> FEATURE:
<221> NAME/KEY: misc_feature
<222> LOCATION: (10)..(10)
<223> OTHER INFORMATION: Xaa is Leu, Ser, Thr, Trp, His, Phe, Asp, Val,
      Glu, or Ala
<220> FEATURE:
<221> NAME/KEY: misc_feature
<222> LOCATION: (16)..(16)
<223> OTHER INFORMATION: Xaa is Gly, Asp, Glu, Gln, Asn, Lys, Arg, or
      Cys
<220> FEATURE:
<221> NAME/KEY: misc_feature
<222> LOCATION: (17)..(17)
<223> OTHER INFORMATION: Xaa is His, Asp, Lys, Glu, or Gln
<220> FEATURE:
<221> NAME/KEY: misc_feature
<222> LOCATION: (18)..(18)
<223> OTHER INFORMATION: Xaa is Glu, His, Ala, or Lys
<220> FEATURE:
```

```
<221> NAME/KEY: misc_feature
<222> LOCATION: (19)..(19)
<223> OTHER INFORMATION: Xaa is Asp, Lys, Glu, or His
<220> FEATURE:
<221> NAME/KEY: misc_feature
<222> LOCATION: (21)..(21)
<223> OTHER INFORMATION: Xaa is Ala, Glu, His, Phe, Tyr, Trp, Arg, or
      Lys
<220> FEATURE:
<221> NAME/KEY: misc_feature
<222> LOCATION: (24)..(24)
<223> OTHER INFORMATION: Xaa is Ala, Glu, Asp, Ser, or His
<220> FEATURE:
<221> NAME/KEY: misc_feature
<222> LOCATION: (27)..(27)
<223> OTHER INFORMATION: Xaa is Asp, Arg, Val, Lys, Ala, Gly, or Glu
<220> FEATURE:
<221> NAME/KEY: misc_feature
<222> LOCATION: (28)..(28)
<223> OTHER INFORMATION: Xaa is Glu, Lys, or Asp
<220> FEATURE:
<221> NAME/KEY: misc_feature
<222> LOCATION: (29)..(29)
<223> OTHER INFORMATION: Xaa is Thr, Ser, Lys, Arg, Trp, Tyr, Phe, Asp,
      Gly, Pro, His, or Glu
<220> FEATURE:
<221> NAME/KEY: misc_feature
<222> LOCATION: (30)..(30)
<223> OTHER INFORMATION: Xaa is Arg, Glu, or His
<220> FEATURE:
<221> NAME/KEY: misc_feature
<222> LOCATION: (31)..(31)
<223> OTHER INFORMATION: Xaa is Lys, Arg, Thr, Ser, Glu, Asp, Trp, Tyr,
      Phe, His, Gly, Gly-Pro, or is deleted

<400> SEQUENCE: 4

Xaa Xaa Glu Gly Xaa Xaa Thr Ser Asp Xaa Ser Ser Tyr Leu Glu Xaa
1               5                   10                  15

Xaa Xaa Xaa Lys Xaa Phe Ile Xaa Trp Leu Xaa Xaa Xaa Xaa Xaa
            20                  25                  30

<210> SEQ ID NO 5
<211> LENGTH: 31
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is L-histidine, D-histidine,
      desaminohistidine, 2-aminohistidine, beta-hydroxyhistidine,
      homohistidine, alpha-fluoromethylhistidine or
      alpha-methylhistidine
<220> FEATURE:
<221> NAME/KEY: misc_feature
<222> LOCATION: (2)..(2)
<223> OTHER INFORMATION: Xaa is Gly, Ala, Val, Leu, Ile, Ser, Met, or
      Thr
<220> FEATURE:
<221> NAME/KEY: misc_feature
<222> LOCATION: (6)..(6)
<223> OTHER INFORMATION: Xaa is His, Trp, Phe, or Tyr
<220> FEATURE:
<221> NAME/KEY: misc_feature
<222> LOCATION: (10)..(10)
<223> OTHER INFORMATION: Xaa is Leu, Ser, Thr, Trp, His, Phe, Asp, Val,
      Glu, or Ala
<220> FEATURE:
<221> NAME/KEY: misc_feature
<222> LOCATION: (16)..(16)
<223> OTHER INFORMATION: Xaa is Gly, Asp, Glu, Gln, Asn, Lys, Arg, or
      Cys
<220> FEATURE:
<221> NAME/KEY: misc_feature
<222> LOCATION: (17)..(17)
<223> OTHER INFORMATION: Xaa is His, Asp, Lys, Glu, or Gln
```

```
<220> FEATURE:
<221> NAME/KEY: misc_feature
<222> LOCATION: (20)..(20)
<223> OTHER INFORMATION: Xaa is Asp, Lys, Glu, or His
<220> FEATURE:
<221> NAME/KEY: misc_feature
<222> LOCATION: (24)..(24)
<223> OTHER INFORMATION: Xaa is Ala, Glu, Asp, Ser, or His
<220> FEATURE:
<221> NAME/KEY: misc_feature
<222> LOCATION: (29)..(29)
<223> OTHER INFORMATION: Xaa is Thr, Ser, Lys, Arg, Trp, Tyr, Phe, Asp,
      Gly, Pro, His, or Glu
<220> FEATURE:
<221> NAME/KEY: misc_feature
<222> LOCATION: (31)..(31)
<223> OTHER INFORMATION: Xaa is Lys, Arg, Thr, Ser, Glu, Asp, Trp, Tyr,
      Phe, His, Gly, Gly-Pro, or is deleted

<400> SEQUENCE: 5

Xaa Xaa Glu Gly Thr Xaa Thr Ser Asp Xaa Ser Ser Tyr Leu Glu Xaa
1               5                   10                  15

Xaa Ala Ala Xaa Glu Phe Ile Xaa Trp Leu Val Lys Xaa Arg Xaa
            20                  25                  30

<210> SEQ ID NO 6
<211> LENGTH: 31
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is L-histidine, D-histidine,
      desaminohistidine, 2-aminohistidine, beta-hydroxyhistidine,
      homohistidine, alpha-fluoromethylhistidine or
      alpha-methylhistidine
<220> FEATURE:
<221> NAME/KEY: misc_feature
<222> LOCATION: (2)..(2)
<223> OTHER INFORMATION: Xaa is Gly, Ala, Val, Leu, Ile, Ser, or Thr
<220> FEATURE:
<221> NAME/KEY: misc_feature
<222> LOCATION: (16)..(16)
<223> OTHER INFORMATION: Xaa is Gly, Asp, Glu, Gln, Asn, Lys, Arg, or
      Cys
<220> FEATURE:
<221> NAME/KEY: misc_feature
<222> LOCATION: (17)..(17)
<223> OTHER INFORMATION: Xaa is His, Asp, Lys, Glu, or Gln
<220> FEATURE:
<221> NAME/KEY: misc_feature
<222> LOCATION: (18)..(18)
<223> OTHER INFORMATION: Xaa is Ala, Glu, His, Phe, Tyr, Trp, Arg, or
      Lys
<220> FEATURE:
<221> NAME/KEY: misc_feature
<222> LOCATION: (24)..(24)
<223> OTHER INFORMATION: Xaa is Ala, Glu, Asp, Ser, or His
<220> FEATURE:
<221> NAME/KEY: misc_feature
<222> LOCATION: (31)..(31)
<223> OTHER INFORMATION: Xaa is Lys, Arg, Thr, Ser, Glu, Asp, Trp, Tyr,
      Phe, His, Gly, Gly-Pro, or is deleted

<400> SEQUENCE: 6

Xaa Xaa Glu Gly Thr Phe Thr Ser Asp Val Ser Ser Tyr Leu Glu Xaa
1               5                   10                  15

Xaa Xaa Ala Lys Glu Phe Ile Xaa Trp Leu Val Lys Gly Arg Xaa
            20                  25                  30

<210> SEQ ID NO 7
<211> LENGTH: 31
```

```
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is L-histidine, D-histidine,
      desaminohistidine, 2-aminohistidine, beta-hydroxyhistidine,
      homohistidine, alpha-fluoromethylhistidine or
      alpha-methylhistidine
<220> FEATURE:
<221> NAME/KEY: misc_feature
<222> LOCATION: (2)..(2)
<223> OTHER INFORMATION: Xaa is Ala, Gly, Val, Thr, Ile, and
      alpha-methylalanine
<220> FEATURE:
<221> NAME/KEY: misc_feature
<222> LOCATION: (15)..(15)
<223> OTHER INFORMATION: Xaa is Glu, Gln, Ala, Thr, Ser, and Gly
<220> FEATURE:
<221> NAME/KEY: misc_feature
<222> LOCATION: (21)..(21)
<223> OTHER INFORMATION: Xaa is Glu, Gln, Ala, Thr, Ser, and Gly
<220> FEATURE:
<221> NAME/KEY: misc_feature
<222> LOCATION: (31)..(31)
<223> OTHER INFORMATION: Xaa is Gly-OH

<400> SEQUENCE: 7

Xaa Xaa Glu Gly Thr Phe Thr Ser Asp Val Ser Ser Tyr Leu Xaa Gly
1               5                   10                  15

Gln Ala Ala Lys Xaa Phe Ile Ala Trp Leu Val Lys Gly Arg Xaa
            20                  25                  30

<210> SEQ ID NO 8
<211> LENGTH: 30
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ala is modified with one of the following
      groups: 4-imidazopropionyl, 4-imidazoacetyl, or
      4-imidazo-alpha,alpha-dimethyl-acetyl
<220> FEATURE:
<221> NAME/KEY: misc_feature
<222> LOCATION: (19)..(19)
<223> OTHER INFORMATION: Xaa is Lys or Arg
<220> FEATURE:
<221> NAME/KEY: MOD_RES
<222> LOCATION: (27)..(27)
<223> OTHER INFORMATION: Lys has a C6-C10 unbranched acyl substituent
      group, or is unsubstituted
<220> FEATURE:
<221> NAME/KEY: MOD_RES
<222> LOCATION: (29)..(29)
<223> OTHER INFORMATION: AMIDATION, if Xaa at 30 is deleted
<220> FEATURE:
<221> NAME/KEY: misc_feature
<222> LOCATION: (30)..(30)
<223> OTHER INFORMATION: Xaa is Gly-OH or is deleted

<400> SEQUENCE: 8

Ala Glu Gly Thr Phe Thr Ser Asp Val Ser Ser Tyr Leu Glu Gly Gln
1               5                   10                  15

Ala Ala Xaa Glu Phe Ile Ala Trp Leu Val Lys Gly Arg Xaa
            20                  25                  30

<210> SEQ ID NO 9
<211> LENGTH: 31
<212> TYPE: PRT
```

```
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is L-histidine, D-histidine,
      desaminohistidine, 2-aminohistidine, beta-hydroxyhistidine,
      homohistidine, alpha-fluoromethylhistidine or
      alpha-methylhistidine
<220> FEATURE:
<221> NAME/KEY: misc_feature
<222> LOCATION: (2)..(2)
<223> OTHER INFORMATION: Xaa is Ala, Gly, Val, Leu, Ile, Ser, or Thr
<220> FEATURE:
<221> NAME/KEY: misc_feature
<222> LOCATION: (6)..(6)
<223> OTHER INFORMATION: Xaa is Phe, Trp, or Tyr
<220> FEATURE:
<221> NAME/KEY: misc_feature
<222> LOCATION: (10)..(10)
<223> OTHER INFORMATION: Xaa is Val, Trp, Ile, Leu, Phe, or Tyr
<220> FEATURE:
<221> NAME/KEY: misc_feature
<222> LOCATION: (12)..(12)
<223> OTHER INFORMATION: Xaa is Ser, Trp, Tyr, Phe, Lys, Ile, Leu, Val
<220> FEATURE:
<221> NAME/KEY: misc_feature
<222> LOCATION: (13)..(13)
<223> OTHER INFORMATION: Xaa is Tyr, Trp, or Phe
<220> FEATURE:
<221> NAME/KEY: misc_feature
<222> LOCATION: (14)..(14)
<223> OTHER INFORMATION: Xaa is Leu, Phe, Tyr, or Trp
<220> FEATURE:
<221> NAME/KEY: misc_feature
<222> LOCATION: (16)..(16)
<223> OTHER INFORMATION: Xaa is Gly, Glu, Asp, or Lys
<220> FEATURE:
<221> NAME/KEY: misc_feature
<222> LOCATION: (19)..(19)
<223> OTHER INFORMATION: Xaa is Ala, Val, Ile, or Leu
<220> FEATURE:
<221> NAME/KEY: misc_feature
<222> LOCATION: (21)..(21)
<223> OTHER INFORMATION: Xaa is Glu, Ile, or Ala
<220> FEATURE:
<221> NAME/KEY: misc_feature
<222> LOCATION: (24)..(24)
<223> OTHER INFORMATION: Xaa is Ala or Glu
<220> FEATURE:
<221> NAME/KEY: misc_feature
<222> LOCATION: (27)..(27)
<223> OTHER INFORMATION: Xaa is Val or Ile
<220> FEATURE:
<221> NAME/KEY: MOD_RES
<222> LOCATION: (30)..(30)
<223> OTHER INFORMATION: AMIDATION, if Xaa at 31 is deleted
<220> FEATURE:
<221> NAME/KEY: misc_feature
<222> LOCATION: (31)..(31)
<223> OTHER INFORMATION: Xaa is Gly, His, NH2, or is deleted

<400> SEQUENCE: 9

Xaa Xaa Glu Gly Thr Xaa Thr Ser Asp Xaa Ser Xaa Xaa Xaa Glu Xaa
1               5                   10                  15

Gln Ala Xaa Lys Xaa Phe Ile Xaa Trp Leu Xaa Lys Gly Arg Xaa
            20                  25                  30

<210> SEQ ID NO 10
<211> LENGTH: 39
<212> TYPE: PRT
<213> ORGANISM: Heloderma sp.
<220> FEATURE:
<221> NAME/KEY: MISC_FEATURE
<222> LOCATION: (39)..(39)
<223> OTHER INFORMATION: Exendin-3
```

```
<220> FEATURE:
<221> NAME/KEY: MOD_RES
<222> LOCATION: (39)..(39)
<223> OTHER INFORMATION: Ser at position 39 may be amidated

<400> SEQUENCE: 10

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Heloderma sp.
<220> FEATURE:
<221> NAME/KEY: MISC_FEATURE
<222> LOCATION: (39)..(39)
<223> OTHER INFORMATION: Exendin-4
<220> FEATURE:
<221> NAME/KEY: MOD_RES
<222> LOCATION: (39)..(39)
<223> OTHER INFORMATION: Ser at position 39 may be amidated

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 12
<211> LENGTH: 31
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is L-histidine, D-histidine,
      desaminohistidine, 2-aminohistidine, beta-hydroxyhistidine,
      homohistidine, alpha-fluoromethylhistidine or
      alpha-methylhistidine
<220> FEATURE:
<221> NAME/KEY: misc_feature
<222> LOCATION: (2)..(2)
<223> OTHER INFORMATION: Xaa is Gly, Ala, or Val
<220> FEATURE:
<221> NAME/KEY: misc_feature
<222> LOCATION: (10)..(10)
<223> OTHER INFORMATION: Xaa is Leu or Val
<220> FEATURE:
<221> NAME/KEY: misc_feature
<222> LOCATION: (12)..(12)
<223> OTHER INFORMATION: Xaa is Lys or Ser
<220> FEATURE:
<221> NAME/KEY: misc_feature
<222> LOCATION: (13)..(13)
<223> OTHER INFORMATION: Xaa is Gln or Tyr
<220> FEATURE:
<221> NAME/KEY: misc_feature
<222> LOCATION: (14)..(14)
<223> OTHER INFORMATION: Xaa is Met or Leu
<220> FEATURE:
<221> NAME/KEY: misc_feature
<222> LOCATION: (16)..(16)
<223> OTHER INFORMATION: Xaa is Glu or Gln
<220> FEATURE:
```

```
<221> NAME/KEY: misc_feature
<222> LOCATION: (17)..(17)
<223> OTHER INFORMATION: Xaa is Glu or Gln
<220> FEATURE:
<221> NAME/KEY: misc_feature
<222> LOCATION: (19)..(19)
<223> OTHER INFORMATION: Xaa is Val or Ala
<220> FEATURE:
<221> NAME/KEY: misc_feature
<222> LOCATION: (20)..(20)
<223> OTHER INFORMATION: Xaa is Arg or Lys
<220> FEATURE:
<221> NAME/KEY: misc_feature
<222> LOCATION: (21)..(21)
<223> OTHER INFORMATION: Xaa is Leu or Glu
<220> FEATURE:
<221> NAME/KEY: misc_feature
<222> LOCATION: (24)..(24)
<223> OTHER INFORMATION: Xaa is Glu or Ala
<220> FEATURE:
<221> NAME/KEY: misc_feature
<222> LOCATION: (27)..(27)
<223> OTHER INFORMATION: Xaa is Val or Lys
<220> FEATURE:
<221> NAME/KEY: misc_feature
<222> LOCATION: (28)..(28)
<223> OTHER INFORMATION: Xaa is Asn or Lys
<220> FEATURE:
<221> NAME/KEY: misc_feature
<222> LOCATION: (30)..(30)
<223> OTHER INFORMATION: Xaa is Gly or Arg
<220> FEATURE:
<221> NAME/KEY: misc_feature
<222> LOCATION: (31)..(31)
<223> OTHER INFORMATION: Xaa is Gly, Pro, Pro-Ser-Ser-Gly-Ala-Pro-
      Pro-Pro-Ser, or is absent

<400> SEQUENCE: 12

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Gly Xaa Xaa
            20                  25                  30

<210> SEQ ID NO 13
<211> LENGTH: 41
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is L-histidine, D-histidine,
      desaminohistidine, 2-aminohistidine, beta-hydroxyhistidine,
      homohistidine, alpha-fluoromethylhistidine or
      alpha-methylhistidine
<220> FEATURE:
<221> NAME/KEY: misc_feature
<222> LOCATION: (2)..(2)
<223> OTHER INFORMATION: Xaa is Ala, Gly, Val, Leu, Ile, Ser, or Thr
<220> FEATURE:
<221> NAME/KEY: misc_feature
<222> LOCATION: (6)..(6)
<223> OTHER INFORMATION: Xaa is Phe, Trp, or Tyr
<220> FEATURE:
<221> NAME/KEY: misc_feature
<222> LOCATION: (10)..(10)
<223> OTHER INFORMATION: Xaa is Val, Trp, Ile, Leu, Phe, or Tyr
<220> FEATURE:
<221> NAME/KEY: misc_feature
<222> LOCATION: (12)..(12)
<223> OTHER INFORMATION: Xaa is Ser, Trp, Tyr, Phe, Lys, Ile, Leu, Val
<220> FEATURE:
<221> NAME/KEY: misc_feature
<222> LOCATION: (13)..(13)
<223> OTHER INFORMATION: Xaa is Tyr, Trp, or Phe
<220> FEATURE:
```

```
<221> NAME/KEY: misc_feature
<222> LOCATION: (14)..(14)
<223> OTHER INFORMATION: Xaa is Leu, Phe, Tyr, or Trp
<220> FEATURE:
<221> NAME/KEY: misc_feature
<222> LOCATION: (16)..(16)
<223> OTHER INFORMATION: Xaa is Gly, Glu, Asp, or Lys
<220> FEATURE:
<221> NAME/KEY: misc_feature
<222> LOCATION: (19)..(19)
<223> OTHER INFORMATION: Xaa is Ala, Val, Ile, or Leu
<220> FEATURE:
<221> NAME/KEY: misc_feature
<222> LOCATION: (21)..(21)
<223> OTHER INFORMATION: Xaa is Glu, Ile, or Ala
<220> FEATURE:
<221> NAME/KEY: misc_feature
<222> LOCATION: (24)..(24)
<223> OTHER INFORMATION: Xaa is Ala or Glu
<220> FEATURE:
<221> NAME/KEY: misc_feature
<222> LOCATION: (27)..(27)
<223> OTHER INFORMATION: Xaa is Val or Ile
<220> FEATURE:
<221> NAME/KEY: misc_feature
<222> LOCATION: (28)..(28)
<223> OTHER INFORMATION: Xaa is Lys, Asp, Arg, or Glu
<220> FEATURE:
<221> NAME/KEY: misc_feature
<222> LOCATION: (30)..(30)
<223> OTHER INFORMATION: Xaa is Gly, Pro, or Arg
<220> FEATURE:
<221> NAME/KEY: misc_feature
<222> LOCATION: (31)..(31)
<223> OTHER INFORMATION: Xaa is Gly, Pro, or Ser
<220> FEATURE:
<221> NAME/KEY: misc_feature
<222> LOCATION: (32)..(32)
<223> OTHER INFORMATION: Xaa is Ser, Pro, or His
<220> FEATURE:
<221> NAME/KEY: misc_feature
<222> LOCATION: (33)..(33)
<223> OTHER INFORMATION: Xaa is Ser, Arg, Thr, Trp, or Lys
<220> FEATURE:
<221> NAME/KEY: misc_feature
<222> LOCATION: (34)..(34)
<223> OTHER INFORMATION: Xaa is Ser or Gly
<220> FEATURE:
<221> NAME/KEY: misc_feature
<222> LOCATION: (35)..(35)
<223> OTHER INFORMATION: Xaa is Ala, Asp, Arg, Glu, Lys, or Gly
<220> FEATURE:
<221> NAME/KEY: MOD_RES
<222> LOCATION: (35)..(41)
<223> OTHER INFORMATION: AMIDATION, if the amino acid immediately
      following is deleted
<220> FEATURE:
<221> NAME/KEY: misc_feature
<222> LOCATION: (36)..(36)
<223> OTHER INFORMATION: Xaa is Pro, Ala, or is absent
<220> FEATURE:
<221> NAME/KEY: MISC_FEATURE
<222> LOCATION: (36)..(40)
<223> OTHER INFORMATION: If Xaa at this position is deleted, then all
      subsequent amino acids are deleted
<220> FEATURE:
<221> NAME/KEY: misc_feature
<222> LOCATION: (37)..(37)
<223> OTHER INFORMATION: Xaa is Pro, Ala, or is absent
<220> FEATURE:
<221> NAME/KEY: misc_feature
<222> LOCATION: (38)..(38)
<223> OTHER INFORMATION: Xaa is Pro, Ala, Arg, Lys, His, or is absent
<220> FEATURE:
<221> NAME/KEY: misc_feature
<222> LOCATION: (39)..(39)
<223> OTHER INFORMATION: Xaa is Ser, His, Pro, Lys, Arg, or is absent
<220> FEATURE:
<221> NAME/KEY: misc_feature
<222> LOCATION: (40)..(40)
```

-continued

```
<223> OTHER INFORMATION: Xaa is His, Ser, Arg, Lys, or is absent
<220> FEATURE:
<221> NAME/KEY: misc_feature
<222> LOCATION: (41)..(41)
<223> OTHER INFORMATION: Xaa is His, Ser, Arg, Lys, or is absent

<400> SEQUENCE: 13

Xaa Xaa Glu Gly Thr Xaa Thr Ser Asp Xaa Ser Xaa Xaa Glu Xaa
1               5                   10                  15

Gln Ala Xaa Lys Xaa Phe Ile Xaa Trp Leu Xaa Xaa Gly Xaa Xaa Xaa
            20                  25                  30

Xaa Xaa Xaa Xaa Xaa Xaa Xaa Xaa Xaa
        35                  40

<210> SEQ ID NO 14
<211> LENGTH: 41
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is L-histidine, D-histidine,
      desaminohistidine, 2-aminohistidine, beta-hydroxyhistidine,
      homohistidine, alpha-fluoromethylhistidine or
      alpha-methylhistidine
<220> FEATURE:
<221> NAME/KEY: misc_feature
<222> LOCATION: (2)..(2)
<223> OTHER INFORMATION: Xaa is Gly, Val, Leu, Ile, Ser, or Thr
<220> FEATURE:
<221> NAME/KEY: misc_feature
<222> LOCATION: (10)..(10)
<223> OTHER INFORMATION: Xaa is Val, Trp, Ile, Leu, Phe, or Tyr
<220> FEATURE:
<221> NAME/KEY: misc_feature
<222> LOCATION: (16)..(16)
<223> OTHER INFORMATION: Xaa is Gly, Glu, Asp, or Lys
<220> FEATURE:
<221> NAME/KEY: misc_feature
<222> LOCATION: (19)..(19)
<223> OTHER INFORMATION: Xaa is Ala, Val, Ile, or Leu
<220> FEATURE:
<221> NAME/KEY: misc_feature
<222> LOCATION: (27)..(27)
<223> OTHER INFORMATION: Xaa is Val or Ile
<220> FEATURE:
<221> NAME/KEY: misc_feature
<222> LOCATION: (28)..(28)
<223> OTHER INFORMATION: Xaa is Lys, Asp, Arg, or Glu
<220> FEATURE:
<221> NAME/KEY: misc_feature
<222> LOCATION: (30)..(30)
<223> OTHER INFORMATION: Xaa is Gly, Pro, or Arg
<220> FEATURE:
<221> NAME/KEY: misc_feature
<222> LOCATION: (31)..(31)
<223> OTHER INFORMATION: Xaa is Gly, Pro, or Ser
<220> FEATURE:
<221> NAME/KEY: misc_feature
<222> LOCATION: (32)..(32)
<223> OTHER INFORMATION: Xaa is Ser, Pro, or His
<220> FEATURE:
<221> NAME/KEY: misc_feature
<222> LOCATION: (33)..(33)
<223> OTHER INFORMATION: Xaa is Ser, Arg, Thr, Trp, or Lys
<220> FEATURE:
<221> NAME/KEY: misc_feature
<222> LOCATION: (34)..(34)
<223> OTHER INFORMATION: Xaa is Ser or Gly
<220> FEATURE:
<221> NAME/KEY: misc_feature
<222> LOCATION: (35)..(35)
<223> OTHER INFORMATION: Xaa is Ala, Asp, Arg, Glu, Lys, or Gly
<220> FEATURE:
```

```
<221> NAME/KEY: misc_feature
<222> LOCATION: (36)..(36)
<223> OTHER INFORMATION: Xaa is Pro or Ala
<220> FEATURE:
<221> NAME/KEY: misc_feature
<222> LOCATION: (37)..(37)
<223> OTHER INFORMATION: Xaa is Pro or Ala
<220> FEATURE:
<221> NAME/KEY: MOD_RES
<222> LOCATION: (37)..(41)
<223> OTHER INFORMATION: AMIDATION, if Xaa at the position immediately
      following is deleted.
<220> FEATURE:
<221> NAME/KEY: misc_feature
<222> LOCATION: (38)..(38)
<223> OTHER INFORMATION: Xaa is Pro, Ala, Arg, Lys, His, or is absent
<220> FEATURE:
<221> NAME/KEY: misc_feature
<222> LOCATION: (38)..(40)
<223> OTHER INFORMATION: If Xaa at this position is deleted, then all
      subsequent amino acids are deleted
<220> FEATURE:
<221> NAME/KEY: misc_feature
<222> LOCATION: (39)..(39)
<223> OTHER INFORMATION: Xaa is Ser, His, Pro, Lys, Arg, or is absent
<220> FEATURE:
<221> NAME/KEY: misc_feature
<222> LOCATION: (40)..(40)
<223> OTHER INFORMATION: Xaa is His, Ser, Arg, Lys, or is absent
<220> FEATURE:
<221> NAME/KEY: misc_feature
<222> LOCATION: (41)..(41)
<223> OTHER INFORMATION: Xaa is His, Ser, Arg, Lys, or is absent

<400> SEQUENCE: 14

Xaa Xaa Glu Gly Thr Phe Thr Ser Asp Xaa Ser Ser Tyr Lys Glu Xaa
1               5                   10                  15

Gln Ala Xaa Lys Glu Phe Ile Ala Trp Leu Xaa Xaa Gly Xaa Xaa Xaa
            20                  25                  30

Xaa Xaa Xaa Xaa Xaa Xaa Xaa Xaa Xaa
            35                  40
```

METHOD FOR ADMINISTERING GLP-1 MOLECULES

CROSS-REFERENCE TO PRIOR APPLICATIONS

This is a U.S. Continuation application of a US Application, claiming the benefit of U.S. Provisional Application No. 60/358,184, filed on Feb. 20, 2002; PCT Application No. PCT/US03/03111 filed on Feb. 7, 2003; and US 371 application Ser. No. 10/504,717 Aug. 17, 2004 now abandoned.

FIELD OF THE INVENTION

The present invention relates to a formulation useful for the oral administration comprising a glucagon-like peptide-1 (GLP-1) compound and a specified delivery agent. Oral administration of the formulations can be used to treat type 2 diabetes as well as a variety of other conditions.

BACKGROUND OF THE INVENTION

Over the past several decades, continuous strides have been made to improve the treatment of diabetes mellitus. Approximately 90% of people with diabetes have type 2 diabetes, also known as non-insulin dependent diabetes mellitus (NIDDM). Type 2 diabetics generally still make insulin, but the insulin cannot be used effectively by the body's cells. This is primarily because the amount of insulin produced in response to rising blood sugar levels is not sufficient to allow cells to efficiently take up glucose and thus, reduce blood sugar levels.

A large body of pre-clinical and clinical research data suggests that glucagon-like peptide-1 (GLP-1) compounds show great promise as a treatment for type 2 diabetes and other conditions. GLP-1 induces numerous biological effects such as stimulating insulin secretion, inhibiting glucagon secretion, inhibiting gastric emptying, enhancing glucose utilization, and inducing weight loss. Further, pre-clinical studies suggest that GLP-1 may also act to prevent the B cell deterioration that occurs as the disease progresses. Perhaps the most salient characteristic of GLP-1 is its ability to stimulate insulin secretion without the associated risk of hypoglycemia that is seen when using insulin therapy or some types of oral therapies that act by increasing insulin expression.

However, development of a GLP-1 therapeutic has been extremely difficult. This is primarily due to the instability of the peptide during manufacturing processes, in solution formulations, and in vivo. The only published clinical studies employing GLP-1 compounds to treat hyperglycemia or other conditions involve formulating GLP-1 compounds such that they can be delivered by subcutaneous injection or through continuous subcutaneous infusion or continuous intravenous administration. Many type 2 diabetics or obese patients desiring to lose weight will not be willing to undertake a treatment regimen that may involve several injections per day. Thus, there is a need to develop GLP-1 compound therapeutics that can be delivered by an alternative non-invasive means such as by oral delivery.

Unfortunately, there are numerous barriers to effective oral delivery of peptides. The high acid content and ubiquitous digestive enzymes of the digestive tract will often degrade proteins and peptides before they reach the site of absorption. Further, many peptides cannot effectively traverse the cells of the epithelial membrane in the small intestine to reach the bloodstream. Finally, many drugs become insoluble at the low pH levels encountered in the digestive tract and, thus, are not absorbed effectively.

The fact that GLP-1 compounds are relatively unstable in solution formulations, only remain in solution under a fairly narrow set of conditions, and have a relatively short in vivo half-life when administered as a solution formulation, suggested that these compounds could not be effectively delivered through the oral route. Thus, it was surprising that GLP-1 compounds could be formulated such that biologically active molecules were absorbed into the blood stream after oral administration.

The present invention involves the use of specific delivery agent molecules that interact with GLP-1 compounds in a non-covalent fashion to allow the compounds to cross gut membranes and yet remain therapeutically active. Although the delivery agents employed in the present invention have been disclosed in a series of U.S. patents (see U.S. Pat. Nos. 5,541,155; 5,693,338; 5,976,569; 5,643,957; 5,955,503; 6,100,298; 5,650,386; 5,866,536; 5,965,121; 5,989,539; 6,001,347; 6,071,510; 5,820,881; and 6,242,495; see also WO 02/02509; WO 01/51454; WO 01/44199; WO 01/32130; WO 00/59863; WO 00/50386; WO 00/47188; and WO 00/40203), oral administration of formulations comprising GLP-1 compounds with these delivery agents has not been disclosed or suggested. Further, numerous parameters impact whether a particular class of compounds can be effectively delivered in combination with one or more classes of delivery agents. For example, the conformation of the peptide, the surface charges on the molecule under certain formulation conditions, the solubility profile, the stability as a formulated component, as well as susceptibility to protease digestion and in vivo stability all influence the ability to deliver a compound orally.

SUMMARY OF THE INVENTION

The present invention encompasses the development of novel formulations comprising GLP-1 compounds and delivery agents that can be administered orally. The present invention provides a formulation which can be administered orally comprising a GLP-1 compound and a specified delivery agent. The GLP-1 compound can be native GLP-1; GLP-1 fragments; GLP-1 analogs; GLP-1 derivatives of native, fragments, or analogs of GLP-1; and Exendin-3 and Exendin-4. The delivery agent is selected from delivery agents described in U.S. Pat. Nos. 5,541,155; 5,693,338; 5,976,569; 5,643,957; 5,955,503; 6,100,298; 5,650,386; 5,866,536; 5,965,121; 5,989,539, 6,001,347; 6,071,510; 5,820,881; and 6,242,495; and WO 02/02509; WO 01/51454; WO 01/44199; WO 01/32130; WO 00/59863; WO 00/50386; WO 00/47188; and WO 00/40203.

Preferred GLP-1 compounds are analogs or derivatives of analogs having modifications at one or more of the following positions: 8, 12, 16, 18, 19, 20, 22, 25, 27, 30, 33, and 37 and show increased potency compared with $Val^8$-GLP-1(7-37) OH. Preferred GLP-1 compounds are also described in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. More preferred GLP-1 compounds are described in compounds of SEQ ID NO:2, SEQ ID NO:12, SEQ ID NO:13, and SEQ ID NO:14.

Preferred delivery agents are described in Table 1. More preferred delivery agents are delivery agents corresponding to numbers of Table 1 selected from the group consisting of 1, 2, 4, 5, 6, 9, 10, 11, 13, 14, 15, 20, 21, 22, 23, 24, 26, 28, 30, 31, 35, 36, 38, 39, 40, 41, 42, 43, 44, 46, 51, 52, and 54.

The present invention also encompasses a method of stimulating the GLP-1 receptor in a subject in need of such stimulation, said method comprising the step of administering to the subject an effective amount of the oral formulation described herein. Subjects in need of GLP-1 receptor stimulation include those with non-insulin dependent diabetes and obesity.

DETAILED DESCRIPTION OF THE INVENTION

The three-letter abbreviation code for amino acids used in this specification conforms with the list contained in Table 3 of Annex C, Appendix 2 of the PCT Administrative Instructions and with 37 C.F.R. §1.822(d)(1)(2000).

For purposes of the present invention as disclosed and described herein, the following terms and abbreviations are defined as follows.

The term "formulation" as used herein refers to a GLP-1 compound and a specified delivery agent combined together which can be administered orally such that GLP-1 compound passes through the gut into the systemic circulation and has the ability to bind to the GLP-1 receptor and initiate a signal transduction pathway resulting in insulinotropic activity. The formulation can optionally comprise other agents so long as the GLP-1 retains the ability to bind the GLP-1 receptor.

The term "oral" as used herein refers to delivery of a compound by mouth such that the compound passes through the stomach, small intestine, or large intestine into the systemic circulation.

The term "GLP-1 compound" as used herein refers to polypeptides that include naturally occurring GLP-1 polypeptides (GLP-1(7-37)OH and GLP-1(7-36)NH$_2$), GLP-1 fragments, GLP-1 analogs, GLP-1 derivatives of naturally occurring GLP-1 polypeptides, GLP-1 fragments, or GLP-1 analogs, and Exendin-3 and Exendin-4 that have the ability to bind to the GLP-1 receptor and initiate a signal transduction pathway resulting in insulinotropic activity.

The term "insulinotropic activity" refers to the ability to stimulate insulin secretion in response to elevated glucose levels, thereby causing glucose uptake by cells and decreased plasma glucose levels. For example, insulinotropic activity can be determined using the method described in Example 1. A GLP-1 molecule has insulinotropic activity if islet cells secrete insulin levels in the presence of the GLP-1 molecule above background levels.

The term "DPP IV resistant" refers to GLP-1 molecules that have extended metabolic stability and improved biological activity. For example, DPP IV resistance can be determined using the method described in Example 2. A GLP-1 molecule is DPP IV resistant if in the presence of DPP IV the GLP-1 molecule has extended metabolic stability above that of native GLP-1. DPP IV resistant GLP-1 molecules can have an amino acid change at the DPP IV recognition site (position 8), or DPP IV resistant peptides can have an attached group that restricts the accessibility of the DPP IV to the recognition site, or both.

A "GLP-1 fragment" is a polypeptide obtained after truncation of one or more amino acids from the N-terminus and/or C-terminus of GLP-1(7-37)OH or an analog or derivative thereof. The nomenclature used to describe GLP-1(7-37)OH is also applicable to GLP-1 fragments. For example, GLP-1 (9-36)OH denotes a GLP-1 fragment obtained by truncating two amino acids from the N-terminus and one amino acid from the C-terminus. The amino acids in the fragment are denoted by the same number as the corresponding amino acid in GLP-1(7-37)OH. For example, the N-terminal glutamic acid in GLP-1(9-36)OH is at position 9; position 12 is occupied by phenylalanine; and position 22 is occupied by glycine, as in GLP-1(7-37)OH. For GLP-1(7-36)OH, the glycine at position 37 of GLP-1(7-37)OH is deleted.

A "GLP-1 analog" has sufficient homology to GLP-1(7-37)OH or a fragment of GLP-1(7-37)OH such that the analog has insulinotropic activity. Preferably, a GLP-1 analog has the amino acid sequence of GLP-1(7-37)OH or a fragment thereof, modified so that from one, two, three, four or five amino acids differ from the amino acid in corresponding position of GLP-1(7-37)OH or a fragment of GLP-1(7-37) OH. In the nomenclature used herein to designate GLP-1 compounds, the substituting amino acid and its position is indicated prior to the parent structure. For example, Glu$^{22}$-GLP-1(7-37)OH designates a GLP-1 compound in which the glycine normally found at position 22 of GLP-1(7-37)OH has been replaced with glutamic acid; Val$^8$-Glu$^{22}$-GLP-1(7-37) OH designates a GLP-1 compound in which alanine normally found at position 8 and glycine normally found at position 22 of GLP-1(7-37)OH have been replaced with valine and glutamic acid, respectively.

GLP-1 molecules also include polypeptides in which one or more amino acids have been added to the N-terminus and/or C-terminus of GLP-1(7-37)OH, or fragments or analogs thereof. It is preferred that GLP-1 molecules of this type have up to about thirty-nine amino acids. The amino acids in the "extended" GLP-1 molecule are denoted by the same number as the corresponding amino acid in GLP-1(7-37)OH. For example, for a GLP-1 molecule obtained by adding two amino acids to the N-terminus of GLP-1(7-37)OH, the N-terminal amino acid is located at position 5; and for a GLP-1 molecule obtained by adding one amino acid to the C-terminus of GLP-1(7-37)OH, the C-terminal amino acid is located at position 38. Thus, position 12 is occupied by phenylalanine and position 22 is occupied by glycine in both of these "extended" GLP-1 compounds, as in GLP-1(7-37)OH. Amino acids 1-6 of an extended GLP-1 molecule are preferably the same as or a conservative substitution of the amino acid at the corresponding position of GLP-1(1-37)OH. Amino acids 38-45 of an extended GLP-1 molecule are preferably the same as or a conservative substitution of the amino acid at the corresponding position of glucagon or Exendin-4.

A "GLP-1 derivative" refers to a molecule having the amino acid sequence of GLP-1, a GLP-1 fragment, or a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower allyl is $C_1$-$C_4$ alkyl. Furthermore, one or more side groups, or terminal groups, may be protected by protective groups known to the ordinarily-skilled protein chemist. The α-carbon of an amino acid may be mono- or dimethylated.

For the purposes of the present invention, an in vitro GLP-1 receptor-signaling assay is used to determine whether a particular extended GLP-1 peptide will exhibit insulinotropic activity in vivo. Extended GLP-1 peptides encompassed by the present invention have an in vitro potency that is not less than one-tenth the in vitro potency of the DPP IV resistant GLP-1 analog known as Val$^8$-GLP-1(7-37)OH. More preferably, the extended GLP-1 peptides of the present invention are as potent or more potent than Val$^8$-GLP-1(7-37)OH.

"In vitro potency" as used herein is the measure of the ability of a peptide to activate the GLP-1 receptor in a cell-based assay. Inn vitro potency is expressed as the "EC$_{50}$" which is the effective concentration of compound that results in 50% activity in a single dose-response experiment. For the purposes of the present invention, in vitro potency is determined using a fluorescence assay that employs HEK-293 Aurora CRE-BLAM cells that stably express the human GLP-1 receptor. These HEK-293 cells have stably integrated a DNA vector having a cAMP response element (CRE) driving expression of the β-lactamase (BLAM) gene. The interaction of a GLP-1 agonist with the receptor initiates a signal that results in activation of the cAMP response element and subsequent expression of β-lactamase. The β-lactamase CCF2/AM substrate that emits fluorescence when it is cleaved by β-lactamase (Aurora Biosciences Corp.) can then be added to cells that have been exposed to a specific amount of GLP-1 agonist to provide a measure of GLP-1 agonist potency. The assay is further described in Zlokarnik, et al. (1998) Science 279:84-88 (See also Example 1). The EC$_{50}$ values for the compounds listed in example 1 were determined using the BLAM assay described above by generating a dose response curve using dilutions ranging from 0.00003 nanomolar to 30 nanomolar. Relative in vitro potency values are established by running Val$^8$-GLP-1(7-37)OH as a control and assigning the control a reference value of 1.

The term "delivery agent" refers to molecules in U.S. Pat. Nos. 5,541,155; 5,693,338; 5,976,569; 5,643,957; 5,955,503; 6,100,298; 5,650,386; 5,866,536; 5,965,121; 5,989,539; 6,001,347; 6,071,510; 5,820,881; and 6,242,495; and WO 02/02509; WO 01/51454; WO 01/44199; WO 01/32130; WO 00/59863; WO 00/50386; WO 00/47188; and WO 00/40203. The delivery agents are generally derived from amino acids and are useful in the oral formulations of the present invention. The derived amino acids can also be in the form of poly amino acids, and peptides. An amino acid is any carboxylic acid having at least one free amine group and includes naturally occurring and synthetic amino acids. Poly amino acids are either peptides or two or more amino acids linked by a bond formed by other groups which can be linked, e.g., an ester, anhydride, or an anhydride linkage. Peptides are two or more amino acids joined by a peptide bond. Peptides can vary in length from dipeptides with two amino acids to polypeptides with several hundred amino acids. Preferred peptides include di-peptides, tri-peptides, tetra-peptides, and penta-peptides.

Furthermore, the delivery agents of the present invention are optionally in a salt form. Examples of salts include sodium, hydrochloric acid, sulfuric acid, phosphoric acid, citric acid, acetic acid, sulfate, phosphate, chloride, bromide, iodide, acetate, propionate, hydrobromic acid, sodium hydroxide, potassium hydroxide, ammonium hydroxide, and potassium carbonate.

The various oral formulations of the present invention may optionally encompass a pharmaceutically acceptable buffer. Examples of pharmaceutically acceptable buffers include phosphate buffers such as dibasic sodium phosphate, TRIS, glycylglycine, maleate, sodium acetate, sodium citrate, sodium tartrate, or an amino acid such as glycine, histidine, lysine or arginine. Other pharmaceutically acceptable buffers are known in the art. Preferably, the buffer is selected from the group consisting of phosphate, TRIS, maleate, and glycine. Even more preferably the buffer is TRIS.

Preferably, the TRIS concentration is between about 1 mM and 100 mM. Even more preferably, the concentration is between about 10 mM and about 50 mM, most preferably the buffer is about 20 mM.

The pH of the oral formulations is adjusted to provide stability and to be acceptable for oral administration. Preferably, the pH is adjusted to between about 7.0 and about 9.0, more preferably the pH is between about 7.4 and 8.4. Even more preferably the pH is between about 7.8 and 8.4. Most preferably, the pH is between about 7.8 and 8.1.

The various oral formulations of the present invention may optionally encompass a suspending agent. Some delivery agents require a suspending agent due to their solubility characteristics. An example of a suspending agent is hydroxypropyl-methylcellulose. Preferably, the final concentration of hydroxypropylmethylcellulose is between about 2% and about 10% (weight/volume). Even more preferably, the concentration is between about 2% and about 5% (w/v). Most preferably the concentration is about 3.9% (w/v).

The oral formulations of the present invention may optionally comprise a cosolvent. Some delivery agents require cosolvents due to their solubility characteristics. Examples of cosolvents include ethanol, N-methylpyrrolidone, N,N-dimethylacetamide, N,N-dimethylformamide, glycofurol, ethoxydiol, propylene glycol, polyethylene glycol 300 and polyvinylpyrrolidone. Preferably, the final concentration of the cosolvents is between about 5% and about 30% (volume/volume). Even more preferably, the concentration is between about 10% and about 25% (v/v). Most preferably the concentration is about 20% (v/v).

The oral formulations of the present invention may optionally comprise a preservative. Preservative refers to a compound that is added to the formulation to act as an antimicrobial agent. Among preservatives known in the art as being effective and acceptable in parenteral formulations are phenolic preservatives, alkylparabens, benzyl alcohol, chlorobutanol, resorcinol, and other similar preservatives, and various mixtures thereof. Examples of phenolic derivatives include cresols and phenol or a mixture of cresols and phenol. Examples of cresols include meta-cresol, ortho-cresol, para-cresol, chlorocresol, or mixtures thereof. Alkylparaben refers to a $C_1$ to $C_4$ alkylparaben, or mixtures thereof. Examples of alkylparabens include methylparaben, ethylparaben, propylparaben, or butylparaben. The concentrations must be sufficient to maintain preservative effectiveness by retarding microbial growth. Preferably, the preservative is a phenol derivative. More preferably the preservative is a cresol. Even more preferably the preservative is meta-cresol.

A preferred concentration of a preservative in the final mixture is about 1.0 mg/mL to about 20.0 mg/mL. More preferred ranges of concentration of preservative in the final mixture are about 2.0 mg/mL to about 8.0 mg/mL, about 2.5 mg/mL to about 4.5 mg/mL and about 2.0 mg/mL to about 4.0 mg/mL. A most preferred concentration of preservative in the final mixture is about 3.0 mg/mL.

The oral formulations of the present invention may optionally comprise an isotonicity agent. Isotonicity agents refer to compounds that are tolerated physiologically and impart a suitable tonicity to the formulation to prevent the net flow of water across cell membranes. Examples of such compounds include glycerin, salts, e.g., NaCl, and sugars, e.g., dextrose, mannitol, and sucrose. These compounds are commonly used for such purposes at known concentrations. One or more isotoniicity agents may be added to adjust the ionic strength or tonicity. The preferred isotonicity agent is NaCl. The concentration of the NaCl is preferably between about 10 mM and 200 mM, more preferred is between about 50 mM and 150 mM, and most preferred is about 100 mM.

The administration compositions may alternatively be in the form of a solid, such as a tablet, capsule or particle, such as a powder. Solid dosage forms may be prepared by mixing the solid form of the compound with the solid form of the active agent. Alternatively, a solid may be obtained from a solution of compound and active agent by methods known in the art, such as freeze drying, precipitation, crystallization ad solid dispersion.

GLP-1 Compounds Appropriate for Use in the Present Invention:

The GLP-1 compounds of the present invention can be made by a variety of methods known in the art such as solid-phase synthetic chemistry, purification of GLP-1 molecules from natural sources, recombinant DNA technology, or a combination of these methods. For example, methods for preparing GLP-1 peptides are described in U.S. Pat. Nos. 5,118,666; 5,120,712; 5,512,549; 5,977,071; and 6,191,102.

By custom in the art, the amino terminus of GLP-1(7-37) OH has been assigned number residue 7, and the carboxy-terminus has been assigned number 37. The other amino acids in the polypeptide are numbered consecutively, as shown in SEQ ID NO: 1. For example, position 12 is phenylalanine and position 22 is glycine.

The two naturally occurring truncated GLP-1 peptides are represented in Formula I, SEQ ID NO: 1.

```
Formula I,
                                               SEQ ID NO: 1
His⁷-Ala-Glu-Gly¹⁰-Thr-Phe-Thr-Ser-Asp-Val-Ser- Ser-Tyr-Leu²⁰-Glu-Gly-Gln-Ala-Ala²⁵-Lys-Glu-Phe- Ile-Ala³⁰-Trp-Leu-Val-Lys-Gly³⁵-Arg-Xaa³⁷
``` wherein:
Xaa$^{37}$ is Gly, or —NH$_2$.

Preferably, a GLP-1 compound has the amino acid sequence of SEQ ID NO:1 or is modified so that from one, two, three, four or five amino acids differ from SEQ ID NO:1.

A preferred group of GLP-1 compounds is composed of GLP-1 analogs of Formula I (SEQ ID NO:2).

```
Formula I
                                               (SEQ ID NO: 2)
His-Xaa⁸-Xaa⁹-Gly-Xaa¹¹-Phe-Thr-Xaa¹⁴-Asp-Xaa¹⁶-

Xaa¹⁷-Xaa¹⁸-Xaa¹⁹-Xaa²⁰-Xaa²¹-Xaa²²-Xaa²³-Xaa²⁴-

Xaa²⁵-Xaa²⁶-Xaa²⁷-Phe-Ile-Xaa³⁰-Xaa³¹-Xaa³²-Xaa³³-

Xaa³⁴-Xaa³⁵-Xaa³⁶-Xaa³⁷-Xaa³⁸-Xaa³⁹-Xaa⁴⁰-Xaa⁴¹-

Xaa⁴²-Xaa⁴³-Xaa⁴⁴-Xaa⁴⁵
``` wherein:
Xaa$^8$ is Ala, Gly, Ser, Thr, Leu, Ile, Val, Glu, Asp, or Lys;
Xaa$^9$ is Glu, Asp, or Lys;
Xaa$^{11}$ is Thr, Ala, Gly, Ser, Leu, Ile, Val, Glu, Asp, or Lys;
Xaa$^{14}$ is Ser, Ala, Gly, Thr, Leu, Ile, Val, Glu, Asp, or Lys;
Xaa$^{16}$ is Val, Ala, Gly, Ser, Thr, Leu, Ile, Tyr, Glu, Asp, Trp, or Lys;
Xaa$^{17}$ is Ser, Ala, Gly, Thr, Leu, Ile, Val, Glu, Asp, or Lys;
Xaa$^{18}$ is Ser, Ala, Gly, Thr, Leu, Ile, Val, Glu, Asp, Trp, Tyr, or Lys;
Xaa$^{19}$ is Tyr, Phe, Trp, Glu, Asp, Gln, or Lys;
Xaa$^{20}$ is Leu, Ala, Gly, Ser, Thr, Ile, Val, Glu, Asp, Met, Trp, Tyr, or Lys;
Xaa$^{21}$ is Glu, Asp, or Lys;
Xaa$^{22}$ is Gly, Ala, Ser, Thr, Leu, Ile, Val, Glu, Asp, or Lys;
Xaa$^{23}$ is Gln, Asn, Arg, Glu, Asp, or Lys;
Xaa$^{24}$ is Ala, Gly, Ser. Thr, Leu, Ile, Val, Arg, Glu, Asp, or Lys;
Xaa$^{25}$ is Ala, Gly, Ser, Thr, Leu, Ile, Val, Glu, Asp, or Lys;
Xaa$^{26}$ is Lys, Arg, Gln, Glu, Asp, or His;
Xaa$^{27}$ is Leu, Glu, Asp, or Lys;
Xaa$^{30}$ is Ala, Gly, Ser, Thr, Leu, Ile, Val, Glu, Asp, or Lys;
Xaa$^{31}$ is Trp, Phe, Tyr, Glu, Asp, or Lys;
Xaa$^{32}$ is Leu, Gly, Ala, Ser, Thr, Ile, Val, Glu, Asp, or Lys;
Xaa$^{33}$ is Val, Gly, Ala, Ser, Thr, Leu, Ile, Glu, Asp, or Lys;
Xaa$^{34}$ is Asn, Lys, Arg, Glu, Asp, or His;
Xaa$^{35}$ is Gly, Ala, Ser, Thr, Leu, Ile, Val, Glu, Asp, or Lys;
Xaa$^{36}$ is Gly, Arg, Lys, Glu, Asp, or His;
Xaa$^{37}$ is Pro, Gly, Ala, Ser, Thr, Leu, Ile, Val, Glu, Asp, or Lys, or is deleted;
Xaa$^{38}$ is Ser, Arg, Lys, Glu, Asp, or His, or is deleted;
Xaa$^{39}$ is Ser, Arg, Lys, Glu, Asp, or His, or is deleted;
Xaa$^{40}$ is Gly, Asp, Glu, or Lys, or is deleted;
Xaa$^{41}$ is Ala, Phe, Trp, Tyr, Glu, Asp, or Lys, or is deleted;
Xaa$^{42}$ is Ser, Pro, Lys, Glu, or Asp, or is deleted;
Xaa$^{43}$ is Ser, Pro, Glu, Asp, or Lys, or is deleted;
Xaa$^{44}$ is Gly, Pro, Glu, Asp, or Lys, or is deleted; and
Xaa$^{45}$ is Ala, Ser, Val, Glu, Asp, or Lys, Ala-NH$_2$, Ser-NH$_2$, Val-NH$_2$, Glu-NH$_2$, Asp-NH$_2$, or Lys-NH$_2$, or is deleted;
provided that when the amino acid at position 37, 38, 39, 40, 41, 42, 43, or 44 is deleted, then each amino acid downstream of that amino acid is also deleted.

It is preferred that the GLP-1 compound of formula I contain less than six amino acids that differ from the corresponding amino acid in GLP-1(7-37)OH or Exendin-4. It is more preferred that less than five amino acids differ from the corresponding amino acid in GLP-1(7-37)OH or Exendin-4. It is even more preferred that less than four amino acids differ from the corresponding amino acid in GLP-1(7-37)OH or Exendin-4.

GLP-1 compounds of the present invention include derivatives of formula I such as a C-1-6-ester, or amide, or C-1-6-alkylamide, or C-1-6-dialkylamide thereof. WO99/43706 describes derivatives of GLP-1 compounds of formula I and is incorporated by reference herein in its entirety. The compounds of formula I derivatized as described in WO 99/43706 and underivatized are encompassed by the present invention.

Another preferred group of GLP-1 compounds is composed of GLP-1 analogs of formula II (SEQ ID NO:3):

```
Formula II
                                               (SEQ ID NO: 3)
Xaa⁷-Xaa⁸-Xaa⁹-Gly-Xaa¹¹-Xaa¹²-Thr-Ser-Asp-Xaa¹⁶-

Ser-Xaa¹⁸-Xaa¹⁹-Leu-Glu-Gly-Xaa²³-Xaa²⁴-Ala-Xaa²⁶-

Xaa²⁷-Phe-Ile-Xaa³⁰-Xaa³¹-Leu-Xaa³³-Xaa³⁴-Xaa³⁵-

Xaa³⁶-R³⁷
``` wherein:
Xaa$^7$ is: L-histidine, D-histidine, desamino-histidine, 2-amino-histidine, β-hydroxy-histidine, homohistidine, α-fluoromethyl-histidine or α-methyl-histidine;
Xaa$^8$ is: Gly, Ala, Val, Leu, Ile, Ser, or Thr;
Xaa$^9$ is: Thr, Ser, Arg, Lys, Trp, Phe, Tyr, Glu, or His;
Xaa$^{11}$ is: Asp, Glu, Arg, Thr, Ala, Lys, or His;
Xaa$^{12}$ is: His, Trp, Phe, or Tyr;
Xaa$^{16}$ is: Leu, Ser, Thr, Trp, His, Phe, Asp, Val, Tyr, Glu, or Ala;

Xaa$^{18}$ is: His, Pro, Asp, Glu, Arg, Ser, Ala, or Lys;
Xaa$^{19}$ is: Gly, Asp, Glu, Gln, Asn, Lys, Arg, or Cys;
Xaa$^{23}$ is: His, Asp, Lys, Glu, Gln, or Arg;
Xaa$^{24}$ is: Glu, Arg, Ala, or Lys;
Xaa$^{26}$ is: Trp, Tyr, Phe, Asp, Lys, Glu, or His;
Xaa$^{27}$ is: Ala, Glu, His, Phe, Tyr, Trp, Arg, or Lys;
Xaa$^{30}$ is: Ala, Glu, Asp, Ser, or His;
Xaa$^{31}$ is: Asp, Glu, Ser, Thr, Arg, Trp, or Lys;
Xaa$^{33}$ is: Asp, Arg, Val, Lys, Ala, Gly, or Glu;
Xaa$^{34}$ is: Glu, Lys, or Asp;
Xaa$^{35}$ is: Thr, Ser, Lys, Arg, Trp, Tyr, Phe, Asp, Gly, Pro, His, or Glu;
Xaa$^{36}$ is: Thr, Ser, Asp, Trp, Tyr, Phe, Arg, Glu, or His;
R$^{37}$ is: Lys, Arg, Thr, Ser, Glu, Asp, Trp, Tyr, Phe, His, Gly, Gly-Pro, or is deleted.

Another preferred group of GLP-1 compounds is composed of GLP-1 analogs of Formula III (SEQ ID NO:4):

Formula III
(SEQ ID NO: 4)
Xaa$^7$-Xaa$^8$-Glu-Gly-Xaa$^{11}$-Xaa$^{12}$-Thr-Ser-Asp-Xaa$^{16}$-

Ser-Ser-Tyr-Leu-Glu-Xaa$^{22}$-Xaa$^{23}$-Xaa$^{24}$-Xaa$^{25}$-Lys-

Xaa$^{27}$-Phe-Ile-Xaa$^{30}$-Trp-Leu-Xaa$^{33}$-Xaa$^{34}$-Xaa$^{35}$-

Xaa$^{36}$-R$^{37}$ wherein:
Xaa$^7$ is: L-histidine, D-histidine, desamino-histidine, 2-amino-histidine, β-hydroxy-histidine, homohistidine, α-fluoromethylhistidine or α-methylhistidine;
Xaa$^8$ is: Gly, Ala, Val, Leu, Ile, Ser, or Thr;
Xaa$^{11}$ is: Asp, Glu, Arg, Thr, Ala, Lys, or His;
Xaa$^{12}$ is: His, Trp, Phe, or Tyr;
Xaa$^{16}$ is: Leu, Ser, Thr, Trp, His, Phe, Asp, Val, Glu, or Ala;
Xaa$^{22}$ is: Gly, Asp, Glu, Gln, Asn, Lys, Arg, or Cys;
Xaa$^{23}$ is: His, Asp, Lys, Glu, or Gln;
Xaa$^{24}$ is: Glu, His, Ala, or Lys;
Xaa$^{25}$ is: Asp, Lys, Glu, or His;
Xaa$^{27}$ is: Ala, Glu, His, Phe, Tyr, Trp, Arg, or Lys;
Xaa$^{30}$ is: Ala, Glu, Asp, Ser, or His;
Xaa$^{33}$ is: Asp, Arg, Val, Lys, Ala, Gly, or Glu;
Xaa$^{34}$ is: Glu, Lys, or Asp;
Xaa$^{35}$ is: Thr, Ser, Lys, Arg, Trp, Tyr, Phe, Asp, Gly, Pro, His, or Glu;
Xaa$^{36}$ is: Arg, Glu, or His;
R$^{37}$ is: Lys, Arg, Thr, Ser, Glu, Asp, Trp, Tyr, Phe, His, Gly, Gly-Pro, or is deleted.

Another preferred group of GLP-1 compounds is composed of GLP-1 analogs of Formula IV (SEQ ID NO:5):

Formula IV
(SEQ ID NO: 5)
Xaa$^7$-Xaa$^8$-Glu-Gly-Thr-Xaa$^{12}$-Thr-Ser-Asp-Xaa$^{16}$-Ser- Ser-Tyr-Leu-Glu-Xaa$^{22}$-Xaa$^{23}$-Ala-Ala-Xaa$^{26}$-Glu-Phe- Ile-Xaa$^{30}$-Trp-Leu-Val-Lys-Xaa$^{35}$-Arg-R$^{37}$ wherein:
Xaa$^7$ is: L-histidine, D-histidine, desamino-histidine, 2-amino-histidine, β-hydroxy-histidine, homohistidine, α-fluoromethyl-histidine, or α-methyl-histidine;
Xaa$^8$ is: Gly, Ala, Val, Leu, Ile, Ser, Met, or Thr;
Xaa$^{12}$ is: His, Trp, Phe, or Tyr;
Xaa$^{16}$ is: Leu, Ser, Thr, Trp, His, Phe, Asp, Val, Glu, or Ala;
Xaa$^{22}$ is: Gly, Asp, Glu, Gln, Asn, Lys, Arg, or Cys;
Xaa$^{23}$ is: His, Asp, Lys, Glu, or Gln;
Xaa$^{26}$ is: Asp, Lys, Glu, or His;
Xaa$^{30}$ is: Ala, Glu, Asp, Ser, or His;
Xaa$^{35}$ is: Thr, Ser, Lys, Arg, Trp, Tyr, Phe, Asp, Gly, Pro, His, or Glu;
R$^{37}$ is: Lys, Arg, Thr, Ser, Glu, Asp, Trp, Tyr, Phe, His, Gly, Gly-Pro, or is deleted.

Another preferred group of GLP-1 compounds is composed of GLP-1 analogs of formula V (SEQ ID NO:6):

Formula V
(SEQ ID NO: 6)
Xaa$^7$-Xaa$^8$-Glu-Gly-Thr-Phe-Thr-Ser-Asp-Val-Ser-Ser- Tyr-Leu-Glu-Xaa$^{22}$-Xaa$^{23}$-Xaa$^{24}$-Ala-Lys-Glu-Phe-Ile- Xaa$^{30}$-Trp-Leu-Val-Lys-Gly-Arg-R$^{37}$ wherein:
Xaa$^7$ is: L-histidine, D-histidine, desamino-histidine, 2-amino-histidine, β-hydroxy-histidine, homohistidine, α-fluoromethyl-histidine, or α-methyl-histidine;
Xaa$^8$ is: Gly, Ala, Val, Leu, Ile, Ser, or Thr;
Xaa$^{22}$ is: Gly, Asp, Glu, Gln, Asn, Lys, Arg, or Cys;
Xaa$^{23}$ is: His, Asp, Lys, Glu, or Gln;
Xaa$^{24}$ is: Ala, Glu, His, Phe, Tyr, Trp, Arg, or Lys;
Xaa$^{30}$ is: Ala, Glu, Asp, Ser, or His;
R$^{37}$ is: Lys, Arg, Thr, Ser, Glu, Asp, Trp, Tyr, Phe, His, Gly, Gly-Pro, or is deleted.

Preferred GLP-1 compounds of formula I, II, III, IV, and V comprise GLP-1 analogs or fragments of GLP-1 analogs wherein the analogs or fragments contain an amino acid other than alanine at position 8 (position 8 analogs). It is preferable that these position 8 analogs contain one or more additional changes at positions 9, 11, 12, 16, 18, 22, 23, 24, 26, 27, 30, 31, 33, 34, 35, 36, and 37 compared to the corresponding amino acid of native GLP-1(7-37)OH. It is also preferable that these analogs have 6 or fewer changes compared to the corresponding amino acids in native GLP-1(7-37)OH or GLP-1(7-36)OH. More preferred analogs have 5 or fewer changes compared to the corresponding amino acids in native GLP-1(7-37)OH or GLP-1(7-36)OH or have 4 or fewer changes compared to the corresponding amino acids in native GLP-1(7-37)OH or GLP-1(7-36)OH. It is even more preferable that these analogs have 3 or fewer changes compared to the corresponding amino acids in native GLP-1(7-37)OH or GLP-1(7-36)OH. It is most preferable that these analogs have 2 or fewer changes compared to the corresponding amino acids in native GLP-1(7-37)OH.

Preferred GLP-1 compounds of formula II, III, UV, and V comprise GLP-1 analogs or fragments of GLP-1 analogs in which glycine at position 22 and preferably alanine at position 8 have been replaced with another amino acid.

When position 22 is aspartic acid, glutamic acid, arginine or lysine, position 8 is preferably glycine, valine, leucine, isoleucine, serine, threonine or methionine and more preferably valine or glycine. When position 22 is a sulfonic acid such as cysteic acid, position 8 is preferably glycine, valine, leucine, isoleucine, serine, threonine or methionine and more preferably valine or glycine.

Other preferred GLP-1 compounds include GLP-1 analogs of formula IV (SEQ ID NO:5) wherein the analogs have the sequence of GLP-1(7-37)OH except that the amino acid at position 8 is preferably glycine, valine, leucine, isoleucine, serine, threonine, or methionine and more preferably valine or glycine and position 30 is glutamic acid, aspartic acid, serine, or histidine and more preferably glutamic acid.

Other preferred GLP-1 compounds include GLP-1 analogs of formula IV (SEQ ID NO:5) wherein the analogs have the sequence of GLP-1(7-37)OH except that the amino acid at position 8 is preferably glycine, valine, leucine, isoleucine, serine, threonine, or methionine and more preferably valine or glycine and position 37 is histidine, lysine, arginine, threonine, serine, glutamic acid, aspartic acid, tryptophan, tyrosine, phenylalanine and more preferably histidine.

Other preferred GLP-1 compounds include GLP-1 analogs of formula IV (SEQ ID NO:5) wherein the analogs have the sequence of GLP-1(7-37)OH, except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine and position 23 is lysine, arginine, glutamic acid, aspartic acid, and histidine and more preferably lysine or glutamic acid.

Other preferred GLP-1 compounds include GLP-1 analogs of formula V (SEQ ID NO:6) wherein the analogs have the sequence of GLP-1(7-37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamine acid or lysine and position 27 is alanine, lysine, arginine, tryptophan, tyrosine, phenylalanine, or histidine and more preferably alanine.

Other preferred GLP-1 compounds include GLP-1 analogs of formula II wherein the analogs have the sequence of GLP-1(7-37)OH except that the amino acid at position 8 and one, two, or three amino acids selected from the group consisting of position 9, position 11, position 12, position 16, position 18, position 22, position 23, position 24, position 26, position 27, position 30, position 31, position 33, position 34, position 35, position 36, and position 37, differ from the amino acid at the corresponding position of native GLP-1(7-37)OH.

Other preferred GLP-1 compounds of formula II include: Val$^8$-GLP-1(7-37)OH, Gly$^8$-GLP-1(7-37)OH, Glu$^{22}$-GLP-1(7-37)OH, Asp$^{22}$-GLP-1(7-37)OH, Arg$^{22}$-GLP-1(7-37)OH, Lys$^{22}$-GLP-1(7-37)OH, Cys$^{22}$-GLP-1(7-37)OH, Val$^8$-Glu$^{22}$-GLP-1(7-37)OH, Val$^8$-Asp$^{22}$-GLP-1(7-37)OH, Val$^8$-Arg$^{22}$-GLP-1(7-37)OH, Val$^8$-Lys$^{22}$-GLP-1(7-37)OH, Val$^8$-Cys$^{22}$-GLP-1(7-37)OH, Gly$^8$-Glu$^{22}$-GLP-1(7-37)OH, Gly$^8$-Asp$^{22}$-GLP-1(7-37)OH, Gly$^8$-Arg$^{22}$-GLP-1(7-37)OH, Gly$^8$-Lys$^{22}$-GLP-1(7-37)OH, Gly$^8$-Cys$^{22}$-GLP-1(7-37)OH, Glu$^{22}$-GLP-1(7-36)OH, Asp$^{22}$-GLP-1(7-36)OH, Arg$^{22}$-GLP-1(7-36)OH, Lys$^{22}$-GLP-1(7-36)OH, Cys$^{22}$-GLP-1(7-36)OH, Val$^8$-Glu$^{22}$-GLP-1(7-36)OH, Val$^8$-Asp$^{22}$-GLP-1(7-36)OH, Val$^8$-Arg$^{22}$-GLP-1(7-36)OH, Val$^8$-Lys$^{22}$-GLP-1(7-36)OH, Val$^8$-Cys$^{22}$-GLP-1(7-36)OH, Gly$^8$-Glu$^{22}$-GLP-1(7-36)OH, Gly$^8$-Asp$^{22}$-GLP-1(7-36)OH, Gly$^8$-Arg$^{22}$-GLP-1(7-36)OH, Gly$^8$-Lys$^{22}$-GLP-1(7-36)OH, Gly$^8$-Cys$^{22}$-GLP-1(7-36)OH, Lys$^{23}$-GLP-1(7-37)OH, Val$^8$-Lys$^{23}$-GLP-1(7-37)OH, Gly$^8$-Lys$^{23}$-GLP-1(7-37)OH, His$^{24}$-GLP-1(7-37)OH, Val$^8$-His$^{24}$-GLP-1(7-37)OH, Gly$^8$-His$^{24}$-GLP-1(7-37)OH, Lys$^{24}$-GLP-1(7-37)OH, Val$^8$-Lys$^{24}$-GLP-1(7-37)OH, Glu$^{30}$-GLP-1(7-37)OH, Val$^8$-Glu$^{30}$-GLP-1(7-37)OH, Gly$^8$-Glu$^{30}$-GLP-1(7-37)OH, Asp$^{30}$-GLP-1(7-37)OH, Val$^8$-Asp$^{30}$-GLP-1(7-37)OH, Gly$^8$-Asp-GLP-1(7-37)OH, Glu$^{30}$-GLP-1(7-37)OH, Val$^8$-Glu$^{30}$-GLP-1(7-37)OH, Gly$^8$-Glu$^{30}$-GLP-1(7-37)OH, Tyr$^{30}$-GLP-1(7-37)OH, Val$^8$-Tyr$^{30}$-GLP-1(7-37)OH, Gly$^8$-Tyr$^{30}$-GLP-1(7-37)OH, Ser$^{30}$-GLP-1(7-37)OH, Val$^8$-Ser$^{30}$-GLP-1(7-37)OH, Gly$^8$-Ser$^{30}$-GLP-1(7-37)OH, His$^{30}$-GLP-1(7-37)OH, Val$^8$-His$^{30}$-GLP-1(7-37)OH, Gly$^8$-His$^{30}$-GLP-1(7-37)OH, Glu$^{34}$-GLP-1(7-37)OH, Val$^8$-Glu$^{34}$-GLP-1(7-37)OH, Gly$^8$-Glu$^{34}$-GLP-1(7-37)OH, Ala$^{34}$-GLP-1(7-37)OH, Val$^8$-Ala$^{34}$-GLP-1(7-37)OH, Gly$^8$-Ala$^{34}$-GLP-1(7-37)OH, Gly$^{34}$-GLP-1(7-37)OH, Val$^8$-Gly$^{34}$-GLP-1(7-37)OH, Gly$^8$-Gly$^{34}$-GLP-1(7-37)OH, Ala$^{35}$-GLP-1(7-37)OH, Val$^8$-Ala$^{35}$-GLP-1(7-37)OH, Gly$^8$-Ala$^{35}$-GLP-1(7-37)OH, Lys$^{35}$-GLP-1(7-37)OH, Val$^8$-Lys$^{35}$-GLP-1(7-37)OH, Gly-Lys$^{35}$-GLP-1(7-37)OH, His$^{35}$-GLP-1(7-37)OH, Val$^8$-His$^{35}$-GLP-1(7-37)OH, Gly$^8$-His$^{35}$-GLP-1(7-37)OH, Pro$^{35}$-GLP-1(7-37)OH, Val$^8$-Pro$^{35}$-GLP-1(7-37)OH, Gly$^8$-Pro$^{35}$-GLP-1(7-37)OH, Glu$^{35}$-GLP-1(7-37)OH, Val$^8$-Glu$^{35}$-GLP-1(7-37)OH, Gly$^8$-Glu$^{35}$-GLP-1(7-37)OH, Val$^8$-Ala$^{27}$-GLP-1(7-37)OH, Val$^8$-His$^{37}$-GLP-1(7-37)OH, Val$^8$-Glu$^{22}$-Lys$^{23}$-GLP-1(7-37)OH, Val$^8$-Glu$^{22}$-Glu$^{23}$-GLP-1(7-37)OH, Val$^8$-Glu$^{22}$-Ala$^{27}$-GLP-1(7-37)OH, Val$^8$-Gly$^{34}$-Lys$^{35}$-GLP-1(7-37)OH, Gly$^8$-His$^{37}$-GLP-1(7-37)OH, Val$^8$-Glu$^{22}$-Ala$^{27}$-GLP-1(7-37)OH, Gly$^8$-Glu 2-Ala$^{27}$-GLP-1(7-37)OH, Val$^8$-Lys$^{22}$-Glu$^{23}$-GLP-1(7-37)OH, and Gly$^8$-Lys$^{22}$-Glu$^{23}$-GLP-1(7-37)OH.

Another preferred group of GLP-1 analogs and derivatives for use in the present invention is composed of molecules of formula VI (SEQ ID NO:7)

Formula VI
(SEQ ID NO: 7)
R$_1$-X-Glu-Gly$^{10}$-Thr-Phe-Thr-Ser-Asp$^{15}$-Val-Ser-Ser- Tyr-Leu$^{20}$-Y-Gly-Gln-Ala-Ala$^{25}$-Lys-Z-Phe-Ile-Ala$^{30}$-

Trp-Leu-Val-Lys-Gly$^{35}$-Arg-R$_2$ wherein:
R$^1$ is selected from the group consisting of L-histidine, D-histidine, desamino-histidine, 2-amino-histidine, β-hydroxy-histidine, homohistidine, α-fluoromethyl-histidine, and α-methylhistidine;
X is selected from the group consisting of Ala, Gly, Val, Thr, Ile, and alpha-methyl-Ala;
Y is selected from the group consisting of Glu, Gln, Ala, Thr, Ser, and Gly;
Z is selected from the group consisting of Glu, Gln, Ala, Thr, Ser, and Gly; and
R$_2$ is Gly-OH.

Another preferred group of GLP-1 compounds for use in the present invention is disclosed in WO 91/11457, and consists essentially of GLP-1(7-34), GLP-1(7-35), GLP-1(7-36), or GLP-1(7-37), or the amide form thereof, and pharmaceutically-acceptable salts thereof, having at least one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9;

serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form. Because the enzyme, dipeptidyl-peptidase IV (DPP IV), may be responsible for the observed rapid in vivo inactivation of administered GLP-1, [See, e.g., Mentlein, R., et al., *Eur. J. Biochem.*, 214:829-835 (1993)], GLP-1 analogs and derivatives that are protected from the activity of DPP IV in the context of a fusion protein are preferred, and fusion proteins wherein the GLP-1 compound is $Gly^8$-GLP-1(7-37)OH, $Val^8$-GLP-1(7-37)OH, α-methyl-$Ala^8$-GLP-1(7-37)OH, or $Gly^8$-$Gln^{21}$-GLP-1(7-37)OH are more preferred. Another preferred group of GLP-1 compounds for use in the present invention consists of the compounds of formula VII (SEQ ID NO:8) claimed in U.S. Pat. No. 5,512,549, which is expressly incorporated herein by reference.

Formula VII (SEQ ID NO: 8)

$R_1$-Ala-Glu-$Gly^{10}$-Thr-Phe-Thr-Ser-$Asp^{15}$-Val-Ser-Ser-Tyr-$Leu^{20}$-Glu-Gly-Gln-Ala-$Ala^{25}$-Xaa-Glu-Phe-Ile-$Ala^{30}$-Trp-Leu-Val-Lys-$Gly^{35}$-Arg-$R_3$

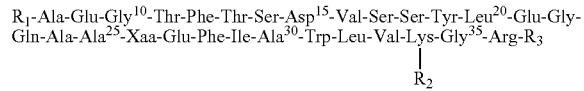

wherein:
$R^1$ is selected from the group consisting of 4-imidazopropionyl, 4-imidazoacetyl, or 4-imidazo-α,α-dimethylacetyl;
$R_2$ is selected from the group consisting of $C_6$-$C_{10}$ unbranched acyl, or is absent;
$R_3$ is selected from the group consisting of Gly-OH or $NH_2$; and
Xaa is Lys or Arg.

More preferred compounds of formula VII for use in the present invention are those in which Xaa is Arg and $R_2$ is $C_6$-$C_{10}$ unbranched acyl. Even more preferred compounds of formula IV for use in the present invention are those in which Xaa is Arg, $R_2$ is $C_6$-$C_{10}$ unbranched acyl, and $R_3$ is Gly-OH. Other highly preferred compounds of formula IV for use in the present invention are those in which Xaa is Arg, $R_2$ is $C_6$-$C_{10}$ unbranched acyl, $R_3$ is Gly-OH, and $R_1$ is 4-imidazopropionyl. An especially preferred compound of formula IV for use in the present invention is that in which Xaa is Arg, $R_2$ is $C_8$ unbranched acyl, $R_3$ is Gly-OH, and $R_1$ is 4-imidazopropionyl.

Other preferred GLP-1 derivatives are described in U.S. Pat. No. 6,268,343 B1. A more preferred GLP-1 derivative is $Arg^{34}Lys^{26}$-(N-ε-(γ-Glu(N-α-hexadecanoyl)))-GLP-1(7-37).

Preferably, the GLP-1 compounds comprise GLP-1 analogs wherein the backbone for such analogs or fragments contains an amino acid other than alanine at position 8 (position 8 analogs). The backbone may also include L-histidine, D-histidine, or modified forms of histidine such as desamino-histidine, 2-amino-histidine, β-hydroxy-histidine, homohistidine, α-fluoromethyl-histidine, or α-methyl-histidine at position 7. It is preferable that these position 8 analogs contain one or more additional changes at positions 12, 16, 18, 19, 20, 22, 25, 27, 30, 33, and 37 compared to the corresponding amino acid of native GLP-1(7-37)OH. It is more preferable that these position 8 analogs contain one or more additional changes at positions 16, 18, 22, 25 and 33 compared to the corresponding amino acid of native GLP-1(7-37)OH.

In a preferred embodiment, the GLP-1 analog is GLP-1(7-37)OH wherein the amino acid at position 12 is selected from the group consisting of tryptophan or tyrosine. It is more preferred that in addition to the substitution at position 12, the amino acid at position 8 is substituted with glycine, valine, leucine, isoleucine, serine, threonine, or methionine and more preferably valine or glycine. It is even more preferred that in addition to the substitutions at position 12 and 8, the amino acid at position 22 is substituted with glutamic acid.

In another preferred embodiment, the GLP-1 analog is GLP-1(7-37)OH wherein the amino acid at position 16 is selected from the group consisting of tryptophan, isoleucine, leucine, phenylalanine, or tyrosine. It is more preferred that in addition to the substitution at position 16, the amino acid at position 8 is substituted with glycine, valine, leucine, isoleucine, serine, threonine, or methionine and more preferably valine or glycine. It is even more preferred that in addition to the substitutions at position 16 and 8, the amino acid at position 22 is substituted with glutamic acid. It is also preferred that in addition to the substitutions at positions 16 and 8, the amino acid at position 30 is substituted with glutamic acid. It is also preferred that in addition to the substitutions at positions 16 and 8, the amino acid at position 37 is substituted with histidine.

In another preferred embodiment, the GLP-1 analog is GLP-1(7-37)OH wherein the amino acid at position 18 is selected from the group consisting of tryptophan, tyrosine, phenylalanine, lysine, leucine, or isoleucine, preferably tryptophan, tyrosine, and isoleucine. It is more preferred that in addition to the substitution at position 18, the amino acid at position 8 is substituted with glycine, valine, leucine, isoleucine, serine, threonine, or methionine and more preferably valine or glycine. It is even more preferred that in addition to the substitutions at position 18 and 8, the amino acid at position 22 is substituted with glutamic acid. It is also preferred that in addition to the substitutions at positions 18 and 8, the amino acid at position 30 is substituted with glutamic acid. It is also preferred that in addition to the substitutions at positions 18 and 8, the amino acid at position 37 is substituted with histidine In another preferred embodiment, the GLP-1 analog is GLP-1(7-37)OH wherein the amino acid at position 19 is selected from the group consisting of tryptophan or phenylalanine, preferably tryptophan. It is more preferred that in addition to the substitution at position 19, the amino acid at position 8 is substituted with glycine, valine, leucine, isoleucine, serine, threonine, or methionine and more preferably valine or glycine. It is even more preferred that in addition to the substitutions at position 19 and 8, the amino acid at position 22 is substituted with glutamic acid. It is also preferred that in addition to the substitutions at positions 19 and 8, the amino acid at position 30 is substituted with glutamic acid. It is also preferred that in addition to the substitutions at positions 19 and 8, the amino acid at position 37 is substituted with histidine In another preferred embodiment, the GLP-1 analog is GLP-1(7-37)OH wherein the amino acid at position 20 is phenylalanine, tyrosine, or tryptophan. It is more preferred that in addition to the substitution at position 20, the amino acid at position 8 is substituted with glycine, valine, leucine, isoleucine, serine, threonine, or methionine and more preferably valine or glycine. It is even more preferred that in addition to the substitutions at position 20 and 8, the amino acid at position 22 is substituted with glutamic acid. It is also preferred that in addition to the substitutions at positions 20 and 8, the amino acid at position 30 is substituted with glutamic acid. It is also preferred that in addition to the substitutions at positions 20 and 8, the amino acid at position 37 is substituted with histidine In another preferred embodiment, the GLP-1 analog is GLP-1(7-37)OH wherein the amino acid at position 25 is selected from the group consisting of valine, isoleucine, and leucine, preferably valine. It is more preferred that in addition to the substitution at position 25, the amino acid at position 8 is substituted with glycine, valine, leucine, isoleucine, serine, threonine, or methionine and more preferably valine or glycine. It is even more preferred that in addition to the substitutions at position 25 and 8, the amino acid at position 22 is substituted with glutamic acid. It is also preferred that in addition to the substitutions at positions 25 and 8, the amino acid at position 30 is substituted with glutamic acid. It is also preferred that in addition to the substitutions at positions 25 and 8, the amino acid at position 37 is substituted with histidine.

In another preferred embodiment, the GLP-1 analog is GLP-1(7-37)OH wherein the amino acid at position 27 is selected from the group consisting of isoleucine or alanine. It is more preferred that in addition to the substitution at position 27, the amino acid at position 8 is substituted with glycine, valine, leucine, isoleucine, serine, threonine, or methionine and more preferably valine or glycine. It is even more preferred that in addition to the substitutions at position 27 and 8, the amino acid at position 22 is substituted with glutamic acid. It is also preferred that in addition to the substitutions at positions 27 and 8, the amino acid at position 30 is substituted with glutamic acid. It is also preferred that in addition to the substitutions at positions 27 and 8, the amino acid at position 37 is substituted with histidine In another preferred embodiment, the GLP-1 analog is GLP-1(7-37)OH wherein the amino acid at position 33 is isoleucine. It is more preferred that in addition to the substitution at position 33, the amino acid at position 8 is substituted with glycine, valine, leucine, isoleucine, serine, threonine, or methionine and more preferably valine or glycine. It is even more preferred that in addition to the substitutions at position 33 and 8, the amino acid at position 22 is substituted with glutamic acid. It is also preferred that in addition to the substitutions at positions 33 and 8, the amino acid at position 30 is substituted with glutamic acid. It is also preferred that in addition to the substitutions at positions 33 and 8, the amino acid at position 37 is substituted with histidine.

The GLP-1 compounds have modifications at one or more of the following positions: 8, 12, 16, 18, 19, 20, 22, 25, 27, 30, 33, and 37. These GLP-1 compounds show increased potency compared with GLP-1(7-37)OH and comprise the amino acid sequence of formula VIII (SEQ ID NO:9)

Formula VIII
(SEQ ID NO: 9)
$Xaa^7$-$Xaa^8$-Glu-Gly-Thr-$Xaa^{12}$-Thr-Ser-Asp-$Xaa^{16}$-Ser- $Xaa^{18}$-$Xaa^{19}$-$Xaa^{20}$-Glu-$Xaa^{22}$-Gln-Ala-$Xaa^{25}$-Lys- $Xaa^{27}$-Phe-Ile-$Xaa^{30}$-Trp-Leu-$Xaa^{33}$-Lys-Gly-Arg-$Xaa^{37}$ wherein:
$Xaa^7$ is: L-histidine, D-histidine, desamino-histidine, 2-amino-histidine, β-hydroxy-histidine, homohistidine, α-fluoromethyl-histidine, or α-methyl-histidine;
$Xaa^8$ is: Ala, Gly, Val, Leu, Ile, Ser, or Thr;
$Xaa^{12}$ is: Phe, Trp, or Tyr;
$Xaa^{16}$ is: Val, Trp, Ile, Leu, Phe, or Tyr;
$Xaa^{18}$ is: Ser, Trp, Tyr, Phe, Lys, Ile, Leu, Val;
$Xaa^{19}$ is: Tyr, Trp, or Phe;
$Xaa^{20}$ is: Leu, Phe, Tyr, or Trp;
$Xaa^{22}$ is: Gly, Glu, Asp, or Lys;
$Xaa^{25}$ is: Ala, Val, Ile, or Leu;
$Xaa^{27}$ is: Glu, Ile, or Ala;
$Xaa^{30}$ is: Ala or Glu;
$Xaa^{33}$ is: Val or Ile; and
$Xaa^{37}$ is: Gly, His, $NH_2$, or is absent.

Some preferred GLP-1 compounds of formula VIII include GLP-1(7-37)OH, GLP-1(7-36)$NH_2$, $Gly^8$-GLP-1(7-37)OH, $Gly^8$-GLP-1(7-36)$NH_2$, $Val^8$-GLP-1(7-37)OH, $Val^8$-GLP-1(7-36)$NH_2$, $Leu^8$-GLP-1(7-37)OH, $Leu^8$-GLP-1(7-36)$NH_2$, $Ile^8$-GLP-1(7-37)OH, $Ile^8$-GLP-1(7-36)$NH_2$, $Ser^8$-GLP-1(7-37)OH, $Ser^8$-GLP-1(7-36)$NH_2$, $Thr^8$-GLP-1(7-37)OH, $Thr^8$-GLP-1(7-36)$NH_2$, $Val^8$-$Tyr^{12}$-GLP-1(7-37)OH, $Val^8$-$Tyr^{12}$-GLP-1(7-36)$NH_2$, $Val^8$-$Tyr^{16}$-GLP-1(7-37)OH, $Val^8$-$Tyr^{16}$-GLP-1(7-36)$NH_2$, $Val^8$-$Glu^{22}$-GLP-1(7-37)OH, $Val^8$-$Glu^{22}$-GLP-1(7-36)$NH_2$, $Gly^8$-$Glu^{22}$-GLP-1(7-37)OH, $Gly^8$-$Glu^{22}$-GLP-1(7-36)$NH_2$, $Val^8$-$Asp^{22}$-GLP-1(7-37)OH, $Val^8$-$Asp^{22}$-GLP-1(7-36)$NH_2$, $Gly^8$-$Asp^{22}$-GLP-1(7-37)OH, $Gly^8$-$Asp^{22}$-GLP-1(7-36)$NH_2$, $Val^8$-$Lys^{22}$-GLP-1(7-37)OH, $Val$-$Lys^{22}$-GLP-1(7-36)$NH_2$, $Gly^8$-$Lys^{22}$-GLP-1(7-37)OH, $Gly^8$-$Lys^{22}$-GLP-1(7-36)$NH_2$, $Leu^8$-$Glu^{22}$-GLP-1(7-37)OH, $Leu^8$-$Glu^{22}$-GLP-1(7-36)$NH_2$, $Ile^8$-$Glu^{22}$-GLP-1(7-37)OH, $Ile^8$-$Glu^{22}$-GLP-1(7-36)$NH_2$, $Leu^8$-$Asp^{22}$-GLP-1(7-37)OH, $Leu^8$-$Asp^{22}$-GLP-1(7-36)$NH_2$, $Ile^8$-$Asp^{22}$-GLP-1(7-37)OH, $Ile^8$-$Asp^{22}$-GLP-1(7-36)$NH_2$, $Leu^8$-$Lys^{22}$-GLP-1(7-37)OH, $Leu^8$-$Lys^{22}$-GLP-1(7-36)$NH_2$, $Ile^8$-$Lys^{22}$-GLP-1(7-37)OH, $Ile^8$-$Lys^{22}$-GLP-1(7-36)$NH_2$, $Ser^8$-$Glu^{22}$-GLP-1(7-37)OH, $Ser^8$-$Glu^{22}$-GLP-1(7-36)$NH_2$, $Thr^8$-$Glu^{22}$-GLP-1(7-37)OH, $Thr^8$-$Glu^{22}$-GLP-1(7-36)$NH_2$, $Ser^8$-$Asp^{22}$-GLP-1(7-37)OH, $Ser^8$-$Asp^{22}$-GLP-1(7-36)$NH_2$, $Thr^8$-$Asp^{22}$-GLP-1(7-37)OH, $Thr^8$-$Asp^{22}$-GLP-1(7-36)$NH_2$, $Ser^8$-$Lys^{22}$-GLP-1(7-37)OH, $Ser^8$-$Lys^{22}$-GLP-1(7-36)$NH_2$, $Thr^8$-$Lys^{22}$-GLP-1(7-37)OH, $Thr^8$-$Lys^{22}$-GLP-1(7-36)$NH_2$, $Glu^{22}$-GLP-1(7-37)OH, $Glu^{22}$-GLP-1(7-36)$NH_2$, $Asp^{22}$-GLP-1(7-37)OH, $Asp^{22}$-GLP-1(7-36)$NH_2$, $Lys^{22}$-GLP-1(7-37)OH, $Lys^{22}$-GLP-1(7-36)$NH_2$, $Val^8$-$Ala^{21}$-GLP-1(7-37)OH, $Val^8$-$Glu^{22}$-$Ala^{27}$-GLP-1(7-37)OH, $Val^8$-$Glu^{30}$-GLP-1(7-37)OH, $Val^8$-$Glu^{30}$-GLP-1(7-36)$NH_2$, $Gly^8$-$Glu^{30}$-GLP-1(7-37)OH, $Gly^8$-$Glu^{30}$-GLP-1(7-36)$NH_2$, $Leu^8$-$Glu^{30}$-GLP-1(7-37)OH, $Leu^8$-$Glu^{30}$-GLP-1(7-36)$NH_2$, $Ile^8$-$Glu^{30}$-GLP-1(7-37)OH, $Ile^8$-$Glu^{30}$-GLP-1(7-36)$NH_2$, $Ser^8$-$Glu^{30}$-GLP-1(7-37)OH, $Ser^8$-$Glu^{30}$-GLP-1(7-36)$NH_2$, $Thr^8$-$Glu^{30}$-GLP-1(7-37)OH, $Thr^8$-$Glu^{30}$-GLP-1(7-36)$NH_2$, $Val^8$-$His^{37}$-GLP-1(7-37)OH, $Val^8$-$His^{37}$-GLP-1(7-36)$NH_2$, $Gly^8$-$His^{37}$-GLP-1(7-37)OH, $Gly^8$-$His^{37}$-GLP-1(7-36)$NH_2$, $Leu^8$-$His^{37}$-GLP-1(7-37)OH, $Leu^8$-$His^{37}$-GLP-1(7-36)$NH_2$, $Ile^8$-$His^{37}$-GLP-1(7-37)OH, $Ile^8$-$His^{37}$-GLP-1(7-36)$NH_2$, $Ser^8$-$His^{37}$-GLP-1(7-37)OH, $Ser^8$-$His^{37}$-GLP-1(7-36)$NH_2$, $Thr^8$-$His^{37}$-GLP-1(7-37)OH, $Thr^8$-$His^{37}$-GLP-1(7-36)$NH_2$.

Some preferred GLP-1 compounds of formula VIII having multiple substitutions include GLP-1(7-37)OH wherein position 8 is valine or glycine, position 22 is glutamic acid, position 16 is tyrosine, leucine or tryptophan, position 18 is tyrosine, tryptophan, or isoleucine, position 25 is valine and position 33 is isoleucine. Other preferred GLP-1 compounds include the following: $Val^8$-$Tyr^{16}$-GLP-1(7-37)OH, $Val^8$-$Tyr^{12}$-$Glu^{22}$-GLP-1(7-37)OH, $Val^8$-$Tyr^{16}$-$Phe^{19}$-GLP-1(7-37)OH, $Val^8$-$Tyr^{16}$-$Glu^{22}$-GLP-1(7-37)OH, $Val^8$-$Trp^{16}$-

Glu²²-GLP-1(7-37)OH, Val⁸-Leu¹⁶-Glu²²-GLP-1(7-37)OH, Val⁸-Ile¹⁶-Glu²²-GLP-1(7-37)OH, Val⁸-Phe¹⁶-Glu²²-GLP-1(7-37)OH, Val⁸-Trp¹⁸-Glu²²-GLP-1(7-37)OH, Val⁸-Tyr¹⁸-Glu²²-GLP-1(7-37)OH, Val⁸-Phe¹⁸-Glu²²-GLP-1(7-37)OH, and Val⁸-Ile¹⁸-Glu²²-GLP-1(7-37)OH.

The GLP-1 compounds of the present invention also encompass Exendin compounds. Exendin-3 and Exendin-4 are biologically active peptides first isolated from Helodermatidae lizard venoms and have been shown to bind the GLP-1 receptor and stimulate cAMP-dependent H⁺ production in mammalian parietal cells. Exendin-3 and Exendin-4 are both 39 amino acid peptides which are approximately 53% homologous to GLP-1. They act as potent agonists of GLP-1 activity. Notably, an N-terminally truncated derivative of Exendin, known as Exendin(9-39 amino acids), is an inhibitor of Exendin-3, Exendin-4 and GLP-1.

An Exendin compound typically comprises a polypeptide having the amino acid sequence of Exendin-3, Exendin-4, or an analog or fragment thereof. Exendin-3 and Exendin-4 are disclosed in U.S. Pat. No. 5,424,286.

Exendin-3 has the amino acid sequence of SEQ ID NO:10:

(SEQ ID NO: 10)
His⁷-Ser-Asp-Gly¹⁰-Thr-Phe-Thr-Ser-Asp¹⁵-Leu-Ser-

Lys-Gln-Met²⁰-Glu-Glu-Glu-Ala-Val²⁵-Arg-Leu-Phe-

Ile-Glu³⁰-Trp-Leu-Lys-Asn-Gly³⁵-Gly-Pro-Ser-Ser-

Gly⁴⁰-Ala-Pro-Pro-Pro-Ser⁴⁵-NH₂

Exendin-4 has the amino acid sequence of SEQ ID NO:11:

(SEQ ID NO: 11)
His⁷-Gly-Glu-Gly¹⁰-Thr-Phe-Thr-Ser-Asp¹⁵-Leu-Ser-

Lys-Gln-Met²⁰-Glu-Glu-Glu-Ala-Val²⁵-Arg-Leu-Phe-

Ile-Glu³⁰-Trp-Leu-Lys-Asn-Gly³⁵-Gly-Pro-Ser-Ser-

Gly⁴⁰-Ala-Pro-Pro-Pro-Ser⁴⁵-NH₂

GLP-1 compounds also include Exendin fragments which are polypeptides obtained after truncation of one or more amino acids from the N-terminus and/or C-terminus of Exendin or an Exendin analog. Furthermore, GLP-1 compounds include Exendin polypeptides in which one or more amino acids have been added to the N-terminus and/or C-terminus of Exendin or fragments thereof. Exendin compounds of this type have up to about forty-five amino acids.

GLP-1 compounds also include "Exendin analogs." An Exendin analog has sufficient homology to Exendin-4, Exendin-3, or a fragment thereof such that the analog has insulinotropic activity. The activity of Exendin fragments and/or analogs can be assessed using in vitro assays such as those described in Example 1.

Preferably, an Exendin analog has the amino acid sequence of Exendin-4 or a fragment thereof, modified so that from one, two, three, four or five amino acids differ from the amino acid in corresponding position of Exendin-4 or the fragment of Exendin-4. In the nomenclature used herein to designate Exendin compounds, the substituting amino acid and its position is indicated prior to the parent structure. For example, Val⁸-Exendin-4 designates an Exendin compound in which the glycine normally found at position 8 of Exendin-4 has been replaced with valine.

Another preferred group of GLP-1 compounds is composed of GLP-1/Exendin-4 analogs of formula IX (SEQ ID NO:12).

Formula IX
(SEQ ID NO: 12)
Xaa⁷-Xaa⁸-Glu-Gly-Thr-Phe-Thr-Ser-Asp-Xaa¹⁶-Ser-

Xaa¹⁸-Xaa¹⁹-Xaa²⁰-Glu-Xaa²²-Xaa²³-Ala-Xaa²⁵-Xaa²⁶-

Xaa²⁷-Phe-Ile-Xaa³⁰-Trp-Leu-Xaa³³-Xaa³⁴-Gly-Xaa³⁶-

R³⁷ wherein:
Xaa⁷ is: L-histidine, D-histidine, desamino-histidine, 2-amino-histidine, β-hydroxy-histidine, homohistidine, α-fluoromethyl-histidine or α-methyl-histidine;
Xaa⁸ is: Gly, Ala, or Val;
Xaa¹⁶ is: Leu or Val;
Xaa¹⁸ is Lys or Ser;
Xaa¹⁹ is: Gln or Tyr;
Xaa²⁰ is: Met or Leu;
Xaa²² is: Glu or Gln;
Xaa²³ is: Glu or Gln;
Xaa²⁵ is: Val or Ala;
Xaa²⁶ is: Arg or Lys;
Xaa²⁷ is Leu or Glu;
Xaa³⁰ is: Glu or Ala;
Xaa³³ is: Val or Lys;
Xaa³⁴ is: Asn or Lys;
Xaa³⁶ is: Gly or Arg; and
R³⁷ is: Gly, Pro, Pro-Ser-Ser-Gly-Ala-Pro-Pro-Pro-Ser, or is absent.

Further Exendin-analogs that are useful for the present invention are described in PCT patent publications WO 99/25728 (Beeley, et al.); WO 99/25727 Beeley, et al.); WO 98/05351 (Young, et al.); WO 99/40788 (Young, et al.); WO 99/07404 (Beeley, et al.); and WO 99/43708 (Knudsen, et al.).

Another preferred group of GLP-1 compounds has the amino acid sequence of formula X (SEQ ID NO: 13)

Formula X
(SEQ ID NO: 13)
Xaa⁷-Xaa⁸-Glu-Gly-Thr-Xaa¹²-Thr-Ser-Asp-Xaa¹⁶-Ser-

Xaa¹⁸-Xaa¹⁹-Xaa²⁰-Glu-Xaa²²-Gln-Ala-Xaa²⁵-Lys-

Xaa²⁷-Phe-Ile-Xaa³⁰-Trp-Leu-Xaa³³-Xaa³⁴-Gly-Xaa³⁶-

Xaa³⁷-Xaa³⁸-Xaa³⁹-Xaa⁴⁰-Xaa⁴¹-Xaa⁴²-Xaa⁴³-Xaa⁴⁴-

Xaa⁴⁵-Xaa⁴⁶-Xaa⁴⁷ wherein:
Xaa⁷ is: L-histidine, D-histidine, desamino-histidine, 2-amino-histidine, β-hydroxy-histidine, homohistidine, α-fluoromethyl-histidine, or α-methyl-histidine;
Xaa⁸ is: Ala, Gly, Val, Leu, Ile, Ser, or Thr;
Xaa¹² is: Phe, Trp, or Tyr;
Xaa¹⁶ is: Val, Trp, Ile, Leu, Phe, or Tyr;
Xaa¹⁸ is: Ser, Trp, Tyr, Phe, Lys, Ile, Leu, Val;
Xaa¹⁹ is: Tyr, Trp, or Phe;
Xaa²⁰ is: Leu, Phe, Tyr, or Trp;
Xaa²² is: Gly, Glu, Asp, or Lys;
Xaa²⁵ is: Ala, Val, Ile, or Leu;
Xaa²⁷ is: Glu, Ile, or Ala;
Xaa³⁰ is: Ala or Glu;
Xaa³³ is: Val or Ile;
Xaa³⁴ is: Lys, Asp, Arg, or Glu;
Xaa³⁶ is: Gly, Pro, or Arg;
Xaa³⁷ is: Gly, Pro, or Ser;
Xaa³⁸ is: Ser, Pro, or His;

Xaa³⁹ is: Ser, Arg, Thr, Trp, or Lys;
Xaa⁴⁰ is: Ser or Gly;
Xaa⁴¹ is: Ala, Asp, Arg, Glu, Lys, or Gly;
Xaa⁴² is: Pro, Ala, NH₂, or is absent;
Xaa⁴³ is: Pro, Ala, NH₂, or is absent;
Xaa⁴⁴ is: Pro, Ala, Arg, Lys, His, NH₂, or is absent;
Xaa⁴⁵ is: Ser, His, Pro, Lys, Arg, NH₂ or is absent;
Xaa⁴⁶ is: His, Ser, Arg, Lys, NH₂ or is absent; and
Xaa⁴⁷ is: His, Ser, Arg, Lys, NH₂ or is absent;
provided that if Xaa⁴², Xaa⁴³, Xaa⁴⁴, Xaa⁴⁵, Xaa⁴⁶, or Xaa⁴⁷ is absent each amino acid downstream is absent and further provided that the GLP-1 peptide does not have the following C-terminal amino acid extension beginning at Xaa³⁶: Gly-Pro-Ser-Ser-Gly-Ala-Pro-Pro-Pro-Ser-NH₂.

Another preferred group of GLP-1 compounds has the amino acid sequence of formula XI (SEQ ID NO: 14)

```
Formula XI
                                           (SEQ ID NO: 14)
Xaa⁷-Xaa⁸-Glu-Gly-Thr-Phe-Thr-Ser-Asp-Xaa¹⁶-Ser- Ser-Tyr-Lys-Glu-Xaa²²-Gln-Ala-Xaa²⁵-Lys-Glu-Phe- Ile-Ala-Trp-Leu-Xaa³³-Xaa³⁴-Gly-Xaa³⁶-Xaa³⁷-Xaa³⁸-

Xaa³⁹-Xaa⁴⁰-Xaa⁴¹-Xaa⁴²-Xaa⁴³-Xaa⁴⁴-Xaa⁴⁵-Xaa⁴⁶-

Xaa⁴⁷
``` wherein:
Xaa⁷ is: L-histidine, D-histidine, desamino-histidine, 2-amino-histidine, β-hydroxy-histidine, homohistidine, α-fluoromethyl-histidine, or α-methyl-histidine;
Xaa⁸ is: Gly, Val, Leu, Ile, Ser, or Thr;
Xaa¹⁶ is: Val, Trp, Ile, Leu, Phe, or Tyr;
Xaa²² is: Gly, Glu, Asp, or Lys;
Xaa²⁵ is: Ala, Val, Ile, or Leu;
Xaa³³ is: Val or Ile;
Xaa³⁴ is: Lys, Asp, Arg, or Glu;
Xaa³⁶ is: Gly, Pro, or Arg;
Xaa³⁷ is: Gly, Pro, or Ser;
Xaa³⁸ is: Ser, Pro, or His;
Xaa³⁹ is: Ser, Arg, Thr, Trp, or Lys;
Xaa⁴⁰ is: Ser or Gly;
Xaa⁴¹ is: Ala, Asp, Arg, Glu, Lys, or Gly;
Xaa⁴² is: Pro or Ala;
Xaa⁴³ is: Pro or Ala;
Xaa⁴⁴ is: Pro, Ala, Arg, Lys, His, NH₂, or is absent;
Xaa⁴⁵ is: Ser, His, Pro, Lys, Arg, NH₂ or is absent;
Xaa⁴⁶ is: His, Ser, Arg, Lys, NH₂ or is absent; and
Xaa⁴⁷ is: His, Ser, Arg, Lys, NH₂ or is absent;
provided that if Xaa⁴⁴, Xaa⁴⁵, Xaa⁴⁶, or Xaa⁴⁷ is absent each amino acid downstream is absent and further provided that the GLP-1 peptide does not have the following C-terminal amino acid extension beginning at Xaa³⁶: Gly-Pro-Ser-Ser-Gly-Ala-Pro-Pro-Pro-Ser-NH₂.

Preferred embodiments of formula X and formula XI include GLP-1 compounds that have valine or glycine at position 8 and glutamic acid at position 22.

Delivery Agents Appropriate for Use in the Present Invention:

The delivery agents of the present invention can be made by organic chemistry methods known in the art and as described in WO 90/36480; WO 96/30036; U.S. Pat. No. 5,643,957; U.S. Pat. No. 6,242,495; all of which are herein incorporated by reference.

Many of the delivery agents of the present invention can be readily prepared from amino acids including, but not limited to, aminocaprylic acid, butyrylhydroxaminic acid, aminophenylbutyric acid, aminophenylhexanoic acid, aminophenylpropionic acid, aminosalicylic acid, aminophenylsuccinic acid, aminononanic acid, aminonicotinic acid, aminovalenic acid, aminophenylacetic acid, aminocaproic acid, aminoundecanoic acid, aminoheptanoic acid, aminohydroxybenzoic acid, and aminodecanoic acid.

For example, these delivery agents may be prepared by reacting the single acid with the appropriate agent which reacts with free amino moiety present in the amino acids to form amides. Protecting groups may be used to avoid unwanted side reactions as would be known to those skilled in the art.

The delivery agents may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0-500 mM sodium chloride gradient is employed.

Useful delivery agents in the present invention are described in U.S. Pat. Nos. 5,541,155; 5,693,338; 5,976,569; 5,643,957; 5,955,503; 6,100,298; 5,650,386; 5,866,536; 5,965,121; 5,989,539; 6,001,347; 6,071,510; 5,820,881; and 6,242,495; and WO02/02509; WO01/51454; WO01/44199; WO01/32130; WO00/59863; WO 00/50386; WO 00/47188; and WO 00/40203; and are all herein incorporated by reference. A skilled artisan will also recognize that variations of the delivery agents can be made and used in the present invention.

Examples of delivery agents are described in Table 1. Preferred delivery agents of Table 1 are delivery agent numbers 1, 2, 4, 5, 6, 9, 10, 11, 13, 14, 15, 20, 21, 22, 23, 24, 26, 28, 30, 31, 35, 36, 38, 39, 40, 41, 42, 43, 44, 46, 51, 52, and 54.

TABLE 1

Delivery agents

| Delivery agent # | Structure |
|---|---|
| 1 | 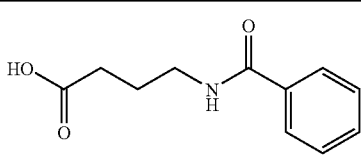 |

TABLE 1-continued

| | Delivery agents |
|---|---|
| Delivery agent # | Structure |
| 2 | 7-(benzoylamino)heptanoic acid |
| 3 | 8-(N-methylbenzoylamino)octanoate |
| 4 | 4-(2-hydroxybenzoylamino)butanoic acid |
| 5 | 7-(2-hydroxybenzoylamino)heptanoic acid |
| 6 | 9-(2-hydroxybenzoylamino)nonanoic acid |
| 7 | N-(6-(dimethylamino)hexyl)-2-hydroxybenzamide |
| 8 | 8-(N-methyl-2-hydroxybenzoylamino)octanoate |
| 9 | 7-(5-chloro-2-hydroxybenzoylamino)heptanoic acid |

TABLE 1-continued

Delivery agents

| Delivery agent # | Structure |
|---|---|
| 10 | (sodium 2-hydroxy-5-chloro-benzamido heptanoate, disodium salt) |
| 11 | (2-hydroxy-3-methyl-benzamido octanoic acid) |
| 12 | (sodium 2-hydroxy-3-methyl-benzamido octanoate, disodium salt) |
| 13 | (4-methoxy-benzamido octanoic acid) |
| 14 | (2-methoxy-4-hydroxy-benzamido octanoic acid) |
| 15 | (4-methoxy-2-hydroxy-benzamido octanoate, disodium salt) |
| 16 | (2-hydroxy-4-methoxy-benzamido-N,N-dimethylhexylamine) |

TABLE 1-continued

Delivery agents

| Delivery agent # | Structure |
|---|---|
| 17 | (Chiral) N-benzoyl-L-tyrosine |
| 18 | 4-[4-(benzoylamino)phenyl]butanoic acid |
| 19 | sodium 4-[4-[methyl(benzoyl)amino]phenyl]butanoate |
| 20 | (Chiral) N-(2-hydroxybenzoyl)-L-phenylalanine |
| 21 | sodium 2-[4-[(2-hydroxybenzoyl)amino]phenyl]acetate |
| 22 | 4-[4-[(2-hydroxybenzoyl)amino]phenyl]butanoic acid |

TABLE 1-continued

| Delivery agent # | Structure |
|---|---|
| 23 | *(structure image)* |
| 24 | *(structure image)* |
| 25 | *(structure image)* |
| 26 | *(structure image)* |
| 27 | *(structure image)* |
| 28 | *(structure image)* |
| 29 | *(structure image)* |
| 30 | *(structure image)* |

TABLE 1-continued
Delivery agents
| Delivery agent # | Structure |
|---|---|
| 31 | 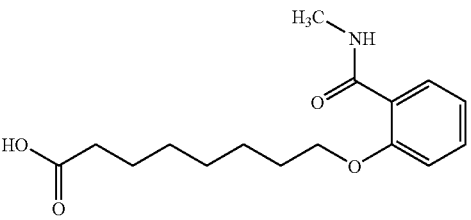 |
| 32 | 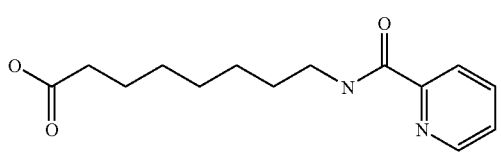 |
| 33 | 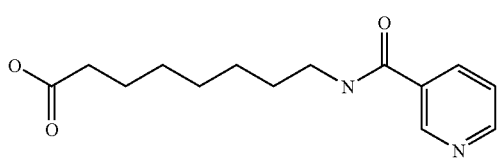 |
| 34 | 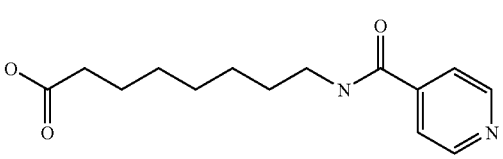 |
| 35 | 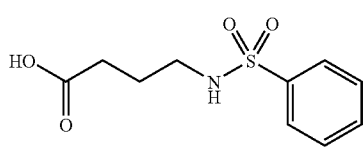 |
| 36 | 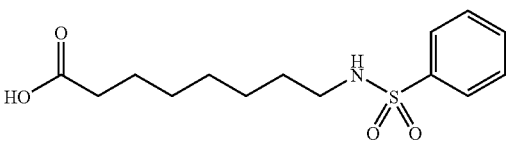 |
| 37 | Chiral 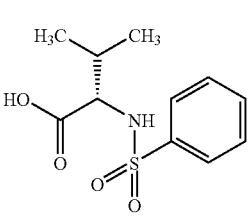 |
| 38 | Chiral 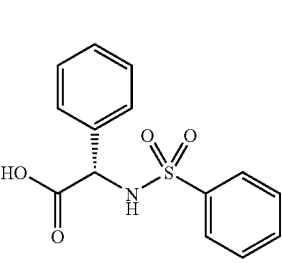 |

TABLE 1-continued

Delivery agents

| Delivery agent # | Structure |
|---|---|
| 39 | *4-(phenylsulfonylamino)benzoic acid* |
| 40 | *4-(4-(phenylsulfonylamino)phenyl)butanoic acid* |
| 41 | *4-(4-(N-methylphenylsulfonamido)phenyl)butanoic acid* |
| 42 | *4-(cyclohexanecarboxamido)butanoic acid* |
| 43 | *8-(cyclohexanecarboxamido)octanoic acid* |
| 44 | *4-(4-(cyclohexanecarboxamido)phenyl)butanoic acid* |
| 45 | Chiral — *N-(cyclohexanecarbonyl)-L-leucine* |

TABLE 1-continued

| Delivery agent # | Structure | |
|---|---|---|
| 46 | (N-cyclohexanecarbonyl-L-phenylalanine structure) | Chiral |
| 47 | (N-cyclohexanecarbonyl-L-tyrosine structure) | Chiral |
| 48 | (N-cyclohexanecarbonyl-L-valine structure) | Chiral |
| 49 | (N-cyclohexanecarbonyl-L-arginine structure) | Chiral |
| 50 | (4-[[(2E)-3-(2-fluorophenyl)-1-oxo-2-propen-1-yl]amino]butanoic acid structure) | |
| 51 | (8-[[(2E)-3-(2-fluorophenyl)-1-oxo-2-propen-1-yl]amino]octanoic acid structure) | |
| 52 | (4-[4-[[(2E)-3-(2-fluorophenyl)-1-oxo-2-propen-1-yl]amino]phenyl]butanoic acid structure) | |

TABLE 1-continued

Delivery agents

| Delivery agent # | Structure |
|---|---|
| 53 | 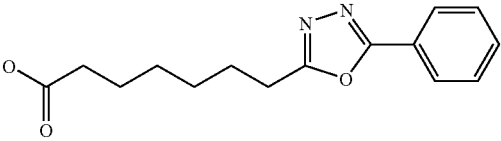 |
| 54 | 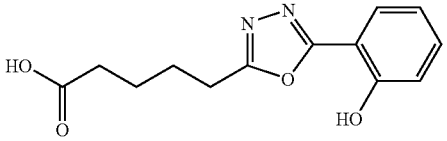 |
| 55 | 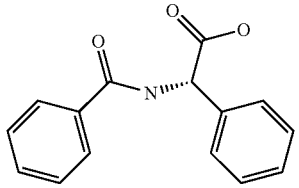 |
| 56 | Chiral 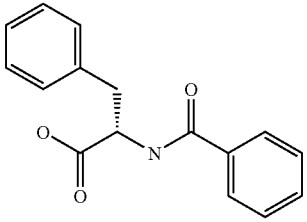 |

The oral formulations comprising a GLP-1 compound and a delivery agent can be used to treat a wide variety of diseases and conditions. The GLP-1 compounds primarily exert their biological effects by acting at a GLP-1 receptor. Subjects with diseases and/or conditions that respond favorably to GLP-1 receptor stimulation or to the administration of GLP-1 compounds can therefore be treated with the oral formulations of the present invention. These subjects are said to "be in need of treatment with GLP-1 compounds" or "in need of GLP-1 receptor stimulation". Included are subjects with non-insulin dependent diabetes, insulin dependent diabetes, stroke (see WO 00/16797), myocardial infarction (see WO 98/08531), obesity (see WO 98/19698), catabolic changes after surgery (see U.S. Pat. No. 6,006,753), functional dyspepsia and irritable bowel syndrome (see WO 99/64060). Also included are subjects requiring prophylactic treatment with a GLP-1 compound, e.g., subjects at risk for developing non-insulin dependent diabetes (see WO 00/07617). Subjects with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

The present invention may be better understood with reference to the following examples. These examples are intended to be representative of specific embodiments of the invention, and are not intended as limiting the scope of the invention.

EXAMPLES

Example 1

Insulinotropic Activity Determination

A collagenase digest of pancreatic tissue is separated on a Ficoll gradient (27%, 23%, 20.5%, and 11% in Hank's balanced salt solution, pH 7.4). The islets are collected from the 20.5%/11% interface, washed and handpicked free of exocrine and other tissue under a stereomicroscope. The islets are incubated overnight in RPMI 1640 medium supplemented with 10% fetal bovine plasma and containing 11 mM glucose at 37° C. and 95% air/5% $CO_2$. The GLP-1 compound to be studied is prepared at a range of concentrations, preferably 3 nanomolar to 30 nanomolar in RPMI medium containing 10% fetal bovine plasma and 16.7 mM glucose. About 8 to 10 isolated islets are then transferred by pipette to a total volume of 250 μL of the GLP-1 compound containing medium in 96-well microtiter dishes. The islets are incubated in the presence of the GLP-1 compound at 37° C., 95% air, 5% $CO_2$ for 90 minutes. Then aliquots of islet-free medium are collected and 100 μl thereof are assayed for the amount of insulin present by radioimmunoassay using an Equate Insulin RIA Kit (Binax, Inc., Portland, Me.).

Example 2

GLP-1 Stability in the Presence of DPP IV

The stability of each GLP-1 molecule can be determined by incubation of the GLP-1 molecule in human plasma. Plasma (800 μL), obtainable from healthy human volunteers, is incubated at 37° C. with 300 pmol/L of a GLP-1 molecule for up to six hours. This is followed by reversed phase HPLC and RIA according to Deacon, et al., in *J. Clin. Endocrinol. Metab.* 80:952-957 (1995).

Example 3

Formulation of Delivery Agent Number 15

Approximately 600 mg of delivery agent number 15 was weighed into Type I glass vials to which 3 mL of base (0.1 N NaOH, pH 12.7) was added to achieve a final concentration of 200 mg/mL. The pH was adjusted to 7.1 and the concentration was estimated to be 171 mg/mL. Delivery agent number 15 was then diluted to 150 mg/mL with Milli-Q® water.

Example 4

Formulation of Delivery Agent Number 40

Delivery agents number 40 and 9 were insoluble at the desired concentration of 150 mg/mL when followed example 1. Further dilution with base to pH 11.5 also did not achieve the desired concentration of 150 mg/mL. Addition of cosolvents also failed to solubilize either delivery agent to the desired concentration of 150 mg/mL. Cosolvents tested included ethanol, N-methylpyrrolidone, N,N-dimethylacetamide, N,N-dimethylformamide, glycofurol, ethoxydiol, propylene glycol, polyethyleneglycol 300, and polyvinylpyrrolidone.

However, for delivery agent number 40, 150 mg was weighed into a Type I vial, to which 1 mL of Milli-Q® water was added, and the pH adjusted with 10 N NaOH. Using this approach, a 150 mg/mL solution was achieved for delivery agent number 40 (pH 8.22).

Example 5

Formulation of Delivery Agent Number 9

Due to the aqueous insolubility of delivery agent number 9, a suspension formulation was prepared in 4% weight/volume (aqueous) of suspending agent hydroxypropylmethylcellulose (Klucel®). Approximately 1.7 mL of suspending agent was added to a Type I glass vial containing 300 mg of delivery agent number 9. The preparation was cooled on ice for 3 minutes, followed by probe sonication on ice for 30 minutes using a Misonix Sonicator® Ultrasonic Processor XL (3/16$^{th}$ inch microtip). Sonication resulted in a reduction of the mean particle size of delivery agent number 9 from 48 μm to 8 μm (Coulter® LS Particle Size Analyzer) at pH 7.98. The formulation was then diluted to 150 mg/mL with the suspending agent.

Example 6

Other Delivery Agents

All other delivery agents were prepared as described in examples 3 and 4 above, except delivery agent numbers 10, 11, 12, 16, 18, 22, 25, 27, 33, and 52, which were prepared as described in example 5 above. Delivery agents 46 and 54 were prepared in two separate formulations: one according to either example 3 or 4 and another according to example 5.

Example 7

Stability Studies

Stability studies were conducted for delivery agent numbers 9, 15, and 40. The delivery agents were freshly prepared as described above respectively to achieve the desired concentration of 150 mg/mL. The samples were divided into three 2 mL aliquots and stored at −20° C., 4° C., and ambient for three days. HPLC assay development and analyses were performed at the end of the storage period. The results are shown in Table 2.

TABLE 2

Stability Data for Delivery agents 9, 15, and 40.

| Temperature | Delivery agent number 40 (mg/mL) | Delivery agent number 15 (mg/mL) | Delivery agent number 9 (mg/mL) |
|---|---|---|---|
| −20° C. | 134.0 | 135.5 | 153.2 |
| 4° C. | 135.1 | 138.2 | 148.6 |
| Ambient | 135.3 | 137.4 | 146.0 |

Example 8

Formulation of the GLP-1 Compound

A solution of Val$^8$-Glu$^{22}$-GLP-1 was prepared by dissolving the GLP-1 compound in distilled water to yield a concentration of 7 mg/mL. The pH was slowly raised to 10.5 with 2 N NaOH, followed by incubation at room temperature for 30 minutes. A volume of 1 M Tris buffer, pH 8.0 was added to give a final buffer concentration 20 mM Tris, and the pH adjusted to pH 7.8 with 1 N or 5 N HCl. The solution was then filtered through a low protein binding 0.22 μM syringe filter (Millex GV, Millipore) and the concentration of the GLP-1 compound was determined by UV spectroscopy. The solution was diluted to a final concentration of 5.5 mg/mL using 20 mM Tris buffer, pH 7.8. The peptide solution was then stored in 1.0 mL aliquots at −70° C. until used.

Example 9

Final Formulations

Final formulations were freshly prepared approximately 30 minutes to 1 hour prior to in vivo dosing by combining 4.5 mL of the delivery agent with 0.5 mL of the GLP-1 compound. The final formulations were dosed by oral gavage at 2 mL/kg (1.1 mg/kg GLP-1 compound, 300 mg/kg delivery agent) with to Male Sprague Dawley rats that were fasted for 12 hours prior to dosing. A subcutaneous dose of the GLP-1 compound alone was used as a control (0.011 mg/kg). The mean pharmacokinetic parameters are shown in the following table.

TABLE 3

Mean Pharmacokinetic Parameters and Bioavailability for Delivery agents 9, 15, and 40.

| Delivery Agent # | Formulation | $T_{max}$ (min) | $C_{max}$ (pg/mL) | AUC (pg * min/mL) | % F[a] |
|---|---|---|---|---|---|
|  | solution | 10 ± 0 | 3781 ± 1097 | 93635 ± 18531 |  |
|  | solution | NC[b] | NC[b] | NC[b] | NC[b] |
| 40 | solution | 6 ± 3 | 6304 ± 4929 | 94215 ± 66732 | 1.01 |
| 15 | solution | 5 ± 0 | 25660 ± 12522 | 254291 ± 129387 | 2.72 |
| 9 | Klucel suspension | 7 ± 3 | 2637 ± 2695 | 28144 ± 38576 | 0.30 |

[a]Bioavailability relative to subcutaneous dosing.
[b]NC = not calculated due below detection level From the above data, the percent bioavailability for the oral administration of Val[8]-Glu[22]-GLP-1 in a formulation with delivery agent number 15 is calculated to be 2.72%, Val[8]-Glu[22]-GLP-1 in a formulation with delivery agent number 40 is calculated to be 1.01%, and Val[8]-Glu[22]-GLP-1 in a formulation with delivery agent number 9 is calculated to be 0.3%.

Pharmacokinetic data for all delivery agents are shown in Table 4, below.

TABLE 4

Tmax, Cmax, and AUC Pharmacokinetic Data for Delivery agents 1 through 56.

| # | Delivery Agent Structure | Peptide | Formulation | Tmax (min) | Cmax (pg/mL) | AUC (pg* min/mL) |
|---|---|---|---|---|---|---|
| A | NA | A[a] | Tris solution | 10 ± 0 | 3781 | 93635 |
| B | NA | B[b] | Tris solution | NC[c] | NC[c] | NC[c] |
| 1 | *(structure)* | A | Tris solution | NC[c] | NC[c] | NC[c] |
| 2 | *(structure)* | A | Tris solution[d] | 5 ± 0 | 875 | 7202 |
| 3 | *(structure)* | A | Tris solution[h] | 5 ± 0 | 24505.8 | 237422.3 |
| 4 | *(structure)* | A | Tris solution | 5 ± 0 | 297.2 | NC[c] |
| 5 | *(structure)* | A | Tris suspension | 5 ± 0 | 4022 | 40984 |

TABLE 4-continued

Tmax, Cmax, and AUC Pharmacokinetic Data for
Delivery agents 1 through 56.

| # | Delivery Agent Structure | Peptide | Formulation | Tmax (min) | Cmax (pg/mL) | AUC (pg* min/mL) |
|---|---|---|---|---|---|---|
| 6 | 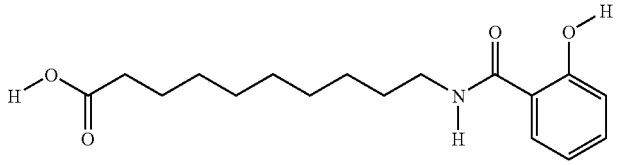 | A | Tris suspension | 5 ± 0 | 3184 | 37926 |
| 7 | 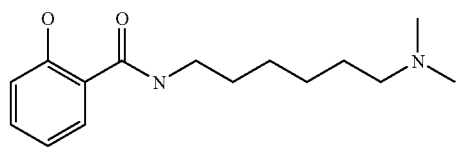 | A | Tris solution | 5 ± 0 | 17576 | 204611 |
| 8 | 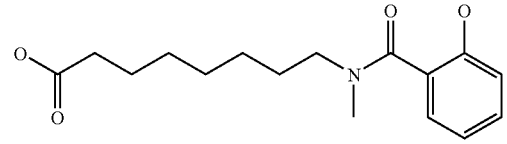 | A | Tris solution | 9 ± 8 | 13247.1 | 173548.6 |
| 9 | 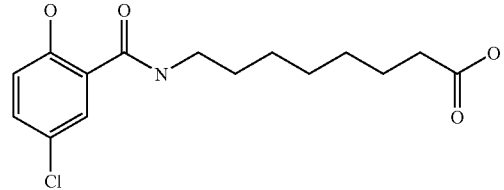 | A | Klucel suspension<br>Klucel suspension | 7 ± 3<br>5 ± 0 | 2637<br>1619 | 28144<br>9889 |
| 10 | 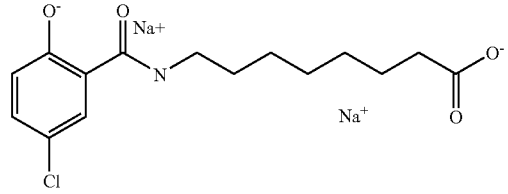 | A | Klucel suspension | NC[c] | NC[c] | NC[c] |
| 11 | 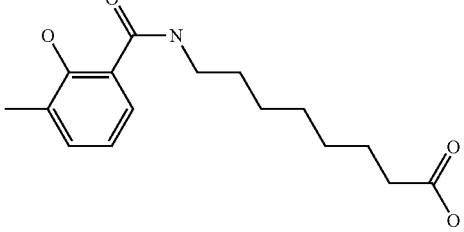 | A | Klucel suspension<br>Klucel suspension | 11 ± 6<br>6 ± 3 | 4760<br>1243.1 | 71350<br>12167.1 |
| 12 | 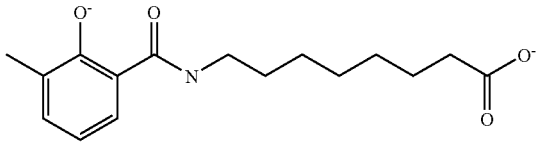 | A | Klucel suspension | 7 ± 3 | 4225 | 35239 |

TABLE 4-continued

Tmax, Cmax, and AUC Pharmacokinetic Data for
Delivery agents 1 through 56.

| # | Delivery Agent Structure | Peptide | Formulation | Tmax (min) | Cmax (pg/mL) | AUC (pg* min/mL) |
|---|---|---|---|---|---|---|
| 13 | | A | Tris suspension[d] | 8 ± 3 | 23297.1 | 279725.0 |
|   | | | Tris suspension[i] | 8 ± 3 | 6265 | 82398 |
| 14 | | A | Tris solution[e] | 6 ± 3 | 12177.9 | 160066.6 |
| 15 | | A | Tris solution | 5 ± 0 | 25660 | 254291 |
| 16 | | A | Klucel suspension | 5 ± 0 | 2113 | 19972 |
| 17 | Chiral | A | Tris solution[h] | NC[c] | NC[c] | NC[c] |
| 18 | | A | Klucel suspension | NC[c] | NC[c] | NC[c] |
| 19 | | A | Tris suspension | 5 ± 0 | 20704.9 | 290106.4 |

TABLE 4-continued

Tmax, Cmax, and AUC Pharmacokinetic Data for
Delivery agents 1 through 56.

| # | Delivery Agent Structure | Peptide | Formulation | Tmax (min) | Cmax (pg/mL) | AUC (pg* min/mL) |
|---|---|---|---|---|---|---|
| 20 | | A | Tris suspension | 5 ± 0 | 1895 | 21948 |
| 21 | | A | Tris suspension | 6 ± 3 | 5833 | 57166 |
| 22 | | A | Klucel suspension | NC[c] | NC[c] | NC[c] |
| 23 | | A | Tris solution[d] | 5 ± 0 | 1930 | 15747 |
| 24 | | A | Tris solution | 13 ± 3 | 1885.3 | 21559.2 |
| 25 | | A | Klucel suspension | NC[c] | NC[c] | NC[c] |
| 26 | | A | Tris solution | 5 ± 0 | 12841.0 | 113480.1 |
| 27 | | A | Klucel suspension[g] | 5 ± 0 | 27898.3 | 299137.2 |

TABLE 4-continued
Tmax, Cmax, and AUC Pharmacokinetic Data for Delivery agents 1 through 56.
| # | Delivery Agent Structure | Peptide | Formulation | Tmax (min) | Cmax (pg/mL) | AUC (pg*min/mL) |
|---|---|---|---|---|---|---|
| 28 | 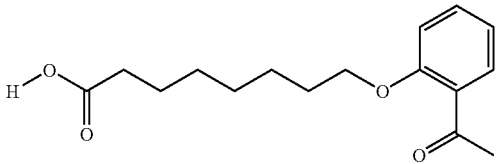 | A | Tris solution<br>Tris suspension | 10 ± 7<br>9 ± 8 | 4220<br>1404 | 59543<br>13116 |
| 29 | 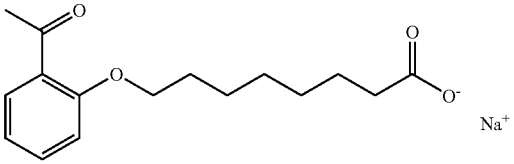 | A | Tris solution | 10 ± 7 | 5262 | 62303 |
| 30 | 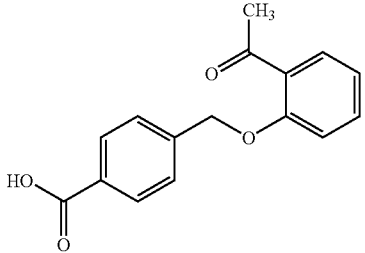 | A | Tris solution | 5 ± 0 | 4174 | 35259 |
| 31 | 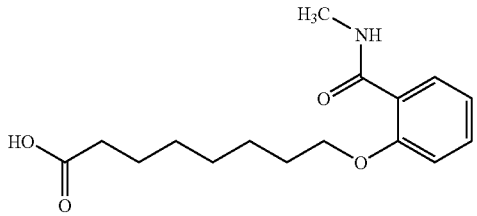 | A | Tris solution | 5 ± 0 | 3724 | 30164 |
| 32 | 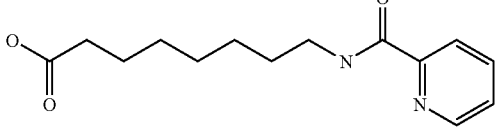 | A | Tris suspension | 6 ± 3 | 10315.9 | 130175.6 |
| 33 | 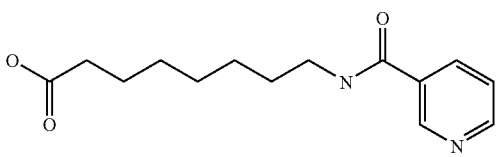 | A | Klucel suspension | 5 ± 0 | 232.1 | NC[c] |
| 34 | 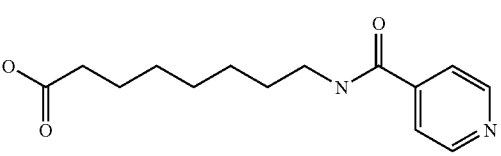 | A | Tris suspension | 9 ± 8 | 756.1 | 6964.2 |
| 35 | 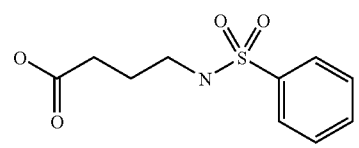 | A | Tris solution | NC[c] | NC[c] | NC[c] |

TABLE 4-continued
Tmax, Cmax, and AUC Pharmacokinetic Data for Delivery agents 1 through 56.
| # | Delivery Agent Structure | Peptide | Formulation | Tmax (min) | Cmax (pg/mL) | AUC (pg* min/mL) |
|---|---|---|---|---|---|---|
| 36 | 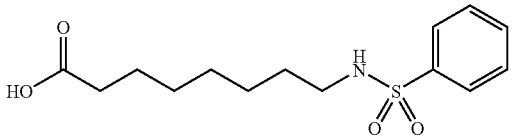 | A | Tris solution | 5 ± 0 | 4752 | 42036 |
| 37 | 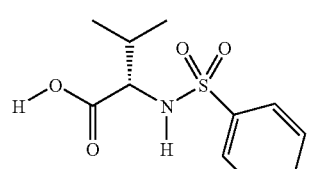 | A | Tris solution | NC[c] | NC[c] | NC[c] |
| 38 | Chiral 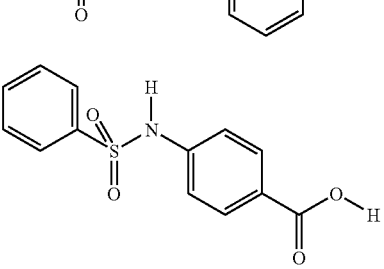 | A | Tris solution | 9 ± 3 | 556 | 5669 |
| 39 | 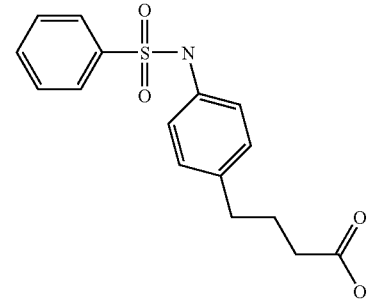 | A | Tris solution | 6 ± 3 | 815 | 6087 |
| 40 | 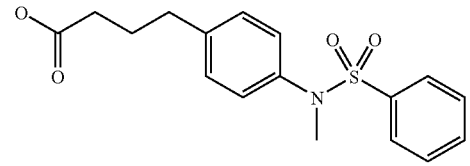 | A | Tris solution | 6 ± 3 | 6304 | 94215 |
| 41 | 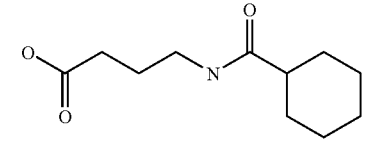 | A | Tris solution | 5 ± 0 | 2117.0 | 21679.1 |
| 42 |  | A | Tris solution | NC[c] | NC[c] | NC[c] |

TABLE 4-continued
Tmax, Cmax, and AUC Pharmacokinetic Data for
Delivery agents 1 through 56.
| # | Delivery Agent Structure | Peptide | Formulation | Tmax (min) | Cmax (pg/mL) | AUC (pg* min/mL) |
|---|---|---|---|---|---|---|
| 43 | 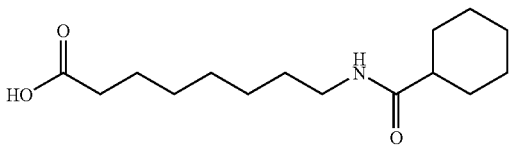 | A | Tris suspension | 5 ± 0 | 962 | 7281 |
| 44 | 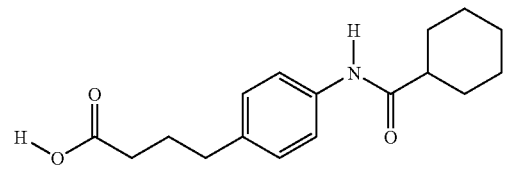 | A | Tris solution | 6 ± 3 | 4227 | 55671 |
| 45 | Chiral 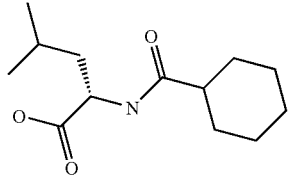 | A | Tris solution[h] | 6 ± 3 | 975.1 | 13468.0 |
| 46 | Chiral 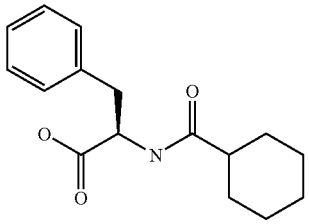 | A | Tris solution<br>Klucel solution | 6 ± 3<br>5 ± 0 | 1746.1<br>544.2 | 19304.1<br>4789.7 |
| 47 | Chiral 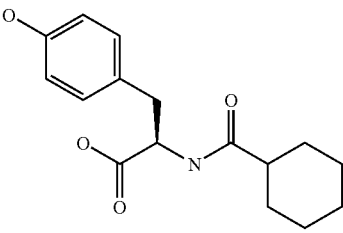 | A | Tris solution | NC[e] | NC[e] | NC[e] |
| 48 | Chiral 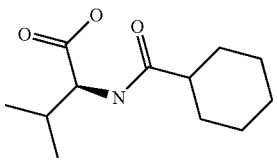 | A | Tris solution | 5 ± 0 | 649.2 | 6068.5 |

TABLE 4-continued

Tmax, Cmax, and AUC Pharmacokinetic Data for
Delivery agents 1 through 56.

| # | Delivery Agent Structure | Peptide | Formulation | Tmax (min) | Cmax (pg/mL) | AUC (pg*min/mL) |
|---|---|---|---|---|---|---|
| 49 | | A | Tris suspension | 5 ± 0 | 165.7 | NC[c] |
| 50 | | A | Tris solution[d] | NC[c] | NC[c] | NC[c] |
| 51 | | A | Tris solution | 5 ± 0 | 1076 | 10838 |
| 52 | | A | Klucel suspension | NC[c] | NC[c] | NC[c] |
| 53 | | A | Tris suspension | 6 ± 3 | 27467 | 337360 |
| 54 | | A | Klucel suspension<br>Tris suspension | 6 ± 3<br>5 ± 0 | 18771.5<br>65729.5 | 218240.8<br>684087.3 |
| 55 | | A | Tris solution | 6 ± 3 | 2398.9 | 20177.7 |

TABLE 4-continued

Tmax, Cmax, and AUC Pharmacokinetic Data for
Delivery agents 1 through 56.

| # | Delivery Agent Structure | Peptide | Formulation | Tmax (min) | Cmax (pg/mL) | AUC (pg* min/mL) |
|---|---|---|---|---|---|---|
| 56 | Chiral | A | Tris solution | 6 ± 3 | 3689.8 | 48324.4 |
| 15 | | B | Tris solution | 5 ± 0 | 8122 | 82656 |

<sup>a</sup>Peptide used: HVEGTFTSDVSSYLEEQAAKEFIAWLVKGRG
<sup>b</sup>Peptide used: HVEGTFTSDVSSYLEEQAAKEFIAWLIKGGPSSGDPPPS
<sup>c</sup>NC not calculated due to insufficient data.
<sup>d</sup>Formulation dosed as a solution with a few undissolved/fibrous particles.
<sup>e</sup>Formulation dosed as a hazy solution.
<sup>f</sup>Formulation dosed as a solution with a few undissolved particles.
<sup>g</sup>Formulation dosed as a hazy viscous solution.
<sup>h</sup>Formulation dosed as a solution with a few translucent particles.
<sup>i</sup>Formulation dosed as a non-homogeneous, somewhat clumpy suspension.

We claim:

1. A composition comprising (i) a GLP-1 compound of SEQ ID NO: 2 and (ii) a delivery agent having the formula

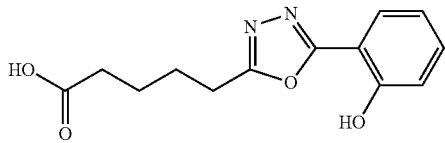

or a pharmaceutically acceptable salt thereof.

2. The composition of claim 1, further comprising an excipient selected from pharmaceutically acceptable buffers, suspending agents, co-solvents, preservatives, isotonicity agents, and combinations thereof.

3. The composition of claim 1, in the form of a tablet, capsule or particle.

4. The composition of claim 1, wherein the GLP-1 compound is a GLP-1 derivative of SEQ ID NO: 2.

* * * * *